United States Patent
Long et al.

(10) Patent No.: US 11,554,204 B2
(45) Date of Patent: *Jan. 17, 2023

(54) SYSTEMS AND METHODS FOR CONTROLLING NEGATIVE PRESSURE THERAPY USING PROPERTIES OF FLUIDS FROM A TISSUE SITE

(71) Applicant: KCI Licensing, Inc., San Antonio, TX (US)

(72) Inventors: Justin Alexander Long, Lago Vista, TX (US); Benjamin Andrew Pratt, Poole (GB); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 27 days.

This patent is subject to a terminal disclaimer.

(21) Appl. No.: 16/961,781

(22) PCT Filed: Jan. 15, 2019

(86) PCT No.: PCT/US2019/013677
§ 371 (c)(1),
(2) Date: Jul. 13, 2020

(87) PCT Pub. No.: WO2019/140448
PCT Pub. Date: Jul. 18, 2019

(65) Prior Publication Data

US 2020/0353137 A1    Nov. 12, 2020

Related U.S. Application Data

(60) Provisional application No. 62/617,517, filed on Jan. 15, 2018.

(51) Int. Cl.
 *A61M 1/00*   (2006.01)
 *A61F 13/00*  (2006.01)
 *A61F 13/02*  (2006.01)

(52) U.S. Cl.
 CPC .......... *A61M 1/73* (2021.05); *A61F 13/0216* (2013.01); *A61M 1/95* (2021.05); *A61M 1/962* (2021.05);
(Continued)

(58) Field of Classification Search
 CPC .... A61F 13/00068; A61F 2013/00944; A61M 1/90; A61M 1/964; A61M 39/24;
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

What is an Electronic Controller? Trerice, Jan. 1, 2001, http://www.cpinc.com/trerice/Control/control_43_44.pdf (Year: 2001).*

(Continued)

*Primary Examiner* — Susan S Su
*Assistant Examiner* — Eric Rassavong

(57) ABSTRACT

Systems, apparatuses, and methods for providing negative pressure and/or instillation fluids to a tissue site are disclosed. Some embodiments are illustrative of an apparatus or system for delivering negative-pressure and/or therapeutic solution of fluids to a tissue site, which can be used in conjunction with sensing properties of fluids extracted from (Continued)

a tissue site and/or instilled at a tissue site. For example, an apparatus may comprise a dressing interface or connector that includes a pH sensor, a humidity sensor, a temperature sensor and/or a pressure sensor embodied on a single pad within the connector and proximate the tissue site to provide data indicative of acidity, humidity, temperature and pressure. Such apparatus may further comprise algorithms for processing such data for detecting leakage and blockage as well as providing information relating to the progression of healing of wounds at the tissue site. An illustrative method may comprise positioning a dressing interface having a pH sensor, a temperature sensor, a humidity sensor, and a pressure sensor at a tissue site, and applying reduced pressure to the dressing interface to draw fluids from the tissue interface in contact with the sensors to sense the pH, temperature, humidity, and pressure properties of the fluids flowing from the tissue site. The method may further comprise providing fluid data indicative of such properties to a processing element for processing the fluid data, and transmitting the data to another component in the system.

17 Claims, 18 Drawing Sheets

(52) U.S. Cl.
CPC ............ *A61M 1/964* (2021.05); *A61M 1/966* (2021.05); *A61F 2013/00944* (2013.01); *A61F 2013/00948* (2013.01); *A61F 2013/00953* (2013.01); *A61F 2013/00957* (2013.01); *A61M 1/92* (2021.05); *A61M 2205/18* (2013.01); *A61M 2205/3553* (2013.01); *A61M 2205/50* (2013.01)

(58) Field of Classification Search
CPC .. A61M 2205/3306; A61M 2205/3344; A61M 2205/3368; A61M 2205/50; A61M 2205/587; A61M 2205/7518; A61M 2205/8206; A61M 1/73; A61M 1/962; A61M 2205/584; A61M 2205/33
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |

(56) References Cited

U.S. PATENT DOCUMENTS

| | | | |
|---|---|---|---|
| 8,529,548 | B2 | 9/2013 | Blott et al. |
| 8,535,296 | B2 | 9/2013 | Blott et al. |
| 8,551,060 | B2 | 10/2013 | Schuessler et al. |
| 8,568,386 | B2 | 10/2013 | Malhi |
| 8,679,081 | B2 | 3/2014 | Heagle et al. |
| 8,834,451 | B2 | 9/2014 | Blott et al. |
| 8,926,592 | B2 | 1/2015 | Blott et al. |
| 9,017,302 | B2 | 4/2015 | Vitaris et al. |
| 9,198,801 | B2 | 12/2015 | Weston |
| 9,211,365 | B2 | 12/2015 | Weston |
| 9,289,542 | B2 | 3/2016 | Blott et al. |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2010/0022990 | A1 | 1/2010 | Karpowicz et al. |
| 2010/0030132 | A1 | 2/2010 | Niezgoda et al. |
| 2014/0005618 | A1* | 1/2014 | Locke ............... A61M 1/962 604/319 |
| 2014/0039424 | A1* | 2/2014 | Locke ............... A61M 1/804 604/319 |
| 2014/0163491 | A1 | 6/2014 | Schuessler et al. |
| 2014/0298927 | A1 | 10/2014 | Allin et al. |
| 2015/0080788 | A1 | 3/2015 | Blott et al. |
| 2015/0100045 | A1* | 4/2015 | Allen .................. A61M 1/82 604/543 |
| 2017/0209641 | A1* | 7/2017 | Mercer ............ A61M 3/0283 |
| 2020/0253786 | A1* | 8/2020 | Harrison .......... A61F 13/00068 |

FOREIGN PATENT DOCUMENTS

| | | | |
|---|---|---|---|
| AU | 755496 | B2 | 12/2002 |
| CA | 2005436 | A1 | 6/1990 |
| DE | 26 40 413 | A1 | 3/1978 |
| DE | 43 06 478 | A1 | 9/1994 |
| DE | 29 504 378 | U1 | 9/1995 |
| EP | 0100148 | A1 | 2/1984 |
| EP | 0117632 | A2 | 9/1984 |
| EP | 0161865 | A2 | 11/1985 |
| EP | 0358302 | A2 | 3/1990 |
| EP | 1018967 | A1 | 7/2000 |
| GB | 692578 | A | 6/1953 |
| GB | 2195255 | A | 4/1988 |
| GB | 2 197 789 | A | 6/1988 |
| GB | 2 220 357 | A | 1/1990 |
| GB | 2 235 877 | A | 3/1991 |
| GB | 2 329 127 | A | 3/1999 |
| GB | 2 333 965 | A | 8/1999 |
| JP | 4129536 | B2 | 8/2008 |
| SG | 71559 | | 4/2002 |
| WO | 80/02182 | A1 | 10/1980 |
| WO | 87/04626 | A1 | 8/1987 |
| WO | 90/010424 | A1 | 9/1990 |
| WO | 93/009727 | A1 | 5/1993 |
| WO | 94/20041 | A1 | 9/1994 |
| WO | 96/05873 | A1 | 2/1996 |
| WO | 97/18007 | A1 | 5/1997 |
| WO | 99/13793 | A1 | 3/1999 |
| WO | 2010/039481 | A1 | 4/2010 |

OTHER PUBLICATIONS

Definition of "Interface" Merriam-Webster Dictionary, https://www.merriam-webster.com/dictionary/interface. Accessed Feb. 8, 2022 (Year: 2022).*
Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman,P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

(56) References Cited

OTHER PUBLICATIONS

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinoví?, V. ?uki?, Ž. Maksimoví?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

International Search Report and Written Opinion for Corresponding Application No. PCT/US2019/013677, dated May 8, 2019.

European Examination Report Corresponding to Application No. 197038417, dated Oct. 11, 2022.

* cited by examiner

SYSTEMS AND METHODS FOR CONTROLLING NEGATIVE PRESSURE THERAPY USING PROPERTIES OF FLUIDS FROM A TISSUE SITE

RELATED APPLICATION

This application claims the benefit, under 35 USC § 119(e), of the filing of U.S. Provisional Patent Application Ser. No. 62/617,517, entitled "SYSTEMS AND METHODS FOR CONTROLLING NEGATIVE PRESSURE THERAPY USING PROPERTIES OF FLUIDS FROM A TISSUE SITE," filed Jan. 15, 2018, which is incorporated herein by reference for all purposes.

TECHNICAL FIELD

The invention set forth in the appended claims relates generally to tissue treatment systems and more particularly, but without limitation, to systems and methods for providing negative-pressure therapy and sensing properties of wound exudates extracted from a tissue site.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound can be washed out with a stream of liquid solution, or a cavity can be washed out using a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and instillation therapy are widely known, improvements to therapy systems, components, and processes may benefit healthcare providers and patients.

BRIEF SUMMARY

New and useful systems, apparatuses, and methods for instilling fluid to a tissue site in a negative-pressure therapy environment are set forth in the appended claims. Illustrative embodiments are also provided to enable a person skilled in the art to make and use the claimed subject matter. Some embodiments are illustrative of an apparatus or system for delivering negative-pressure and therapeutic solution of fluids to a tissue site, which can be used in conjunction with sensing properties of wound exudates extracted from a tissue site. For example, an apparatus may include a pH sensor, a humidity sensor, a temperature sensor and a pressure sensor embodied on a single pad proximate the tissue site to provide data indicative of acidity, humidity, temperature and pressure. Such apparatus may further comprise an algorithm for processing such data for detecting leakage and blockage as well as providing information relating to the progression of healing of wounds at the tissue site.

In some embodiments, for example, a system for treating a tissue site with negative pressure and sensing properties of fluids at the tissue site may comprise a dressing interface for coupling a source of negative-pressure to the tissue site. The dressing interface may comprise a housing having a therapy cavity including an opening configured to be disposed in fluid communication with the tissue site, a negative-pressure port adapted to fluidly couple the therapy cavity to the source of negative-pressure, and a vent port adapted to fluidly couple the therapy cavity to a source of positive-pressure. The dressing interface may further comprise a pressure sensor mounted to the housing in fluid communication with the therapy cavity and configured to sense the pressure of the fluids at the tissue site, a humidity sensor mounted to the housing in fluid communication with the therapy cavity and configured to sense the humidity of the fluids at the tissue site, and a temperature sensor mounted to the housing in fluid communication with the therapy cavity and configured to sense the temperature of the fluids at the tissue site. The dressing interface may further comprise a processing element mounted to the housing outside the therapy cavity and electrically coupled to the pressure sensor, the humidity sensor, and the temperature sensor for receiving property signals indicative of the pressure, humidity, and temperature of the fluid at the tissue site, wherein the processing element may be configured to determine flow characteristics of the system.

In some embodiments, the processing element may further comprise a microprocessor and a transmitter that are configured to process and transmit the property signals for assessing the flow characteristics of the system. The system may further comprise a controller for receiving the property signals from the processing element, wherein the controller is further configured to assess the flow characteristics of the system. The system may be configured to be fluidly coupled to a pump for providing negative-pressure to the dressing interface and the tissue site and may further comprise sensors electrically coupled to the controller to determine a pump pressure and a duty cycle of pressure being provided by the pump. The flow characteristics of the system may include a blockage state condition, and air leak state, a fluid leak state, and/or a desiccation state within the system wherein the controller may be configured to provide an alarm indicative of any one of the states based on the property signals, the pump pressure, and the duty cycle.

In some embodiments, the dressing interface may further comprise a pH sensor mounted to the housing in fluid communication with the therapy cavity and configured to sense the pH of the fluids at the tissue site. The processing element may be electrically coupled to the pH sensor for receiving property signals including a property signal indicative of the pH of the fluid at the tissue site, wherein the processing element may be configured to assess the health characteristics of the tissue site, and may further comprise a microprocessor and a transmitter to process and transmit the property signals for assessing the health characteristics of the tissue site. The system may further comprise a controller for receiving the property signals from the processing element and may be further configured to assess the health characteristics of the tissue site. The health characteristics of the system may include a wound progression state within the system, and the controller may be configured to provide an alarm indicative of the wound progression state based on the property signals.

Some embodiments are illustrative of a method for treating a tissue site with negative pressure and assessing properties of fluids at the tissue site within a system utilizing a dressing interface having a housing including a therapy cavity adapted to be in fluid communication with the tissue site. In some embodiments, the method may comprise sensing pressure of the fluids at the tissue site using a pressure sensor mounted to the housing in fluid communication with the therapy cavity, sensing humidity of the fluids at the tissue site using a humidity sensor mounted to the housing in fluid communication with the therapy cavity, and sensing temperature of the fluids at the tissue site using a temperature sensor mounted to the housing in fluid communication with the therapy cavity. The method may further comprise determining flow characteristics of the system by using a processing element mounted to the housing outside the therapy cavity and electrically coupled to the pressure sensor, the humidity sensor, and the temperature sensor for receiving property signals indicative of the pressure, humidity, and temperature. The method may further comprise sensing a pump pressure and a duty cycle of pressure being provided by a pump for providing negative-pressure to the dressing interface and the tissue site, wherein the pump pressure and the duty cycle are provided by sensors electrically coupled to the controller. The flow characteristics of the system may include a blockage state condition, and air leak state, a fluid leak state, and/or a desiccation state within the system to provide an alarm indicative of any one of the states based on the property signals, the pump pressure, and the duty cycle. The method may further comprise sensing pH of the fluids at the tissue site using a pH sensor mounted to the housing in fluid communication with the therapy cavity and determining health characteristics of the tissue site by using a processing element mounted to the housing outside the therapy cavity and electrically coupled to the pH sensor for receiving property signals indicative of the pH.

Some embodiments are illustrative of a method for treating a tissue site with negative pressure and assessing properties of fluids at the tissue site within a system utilizing a dressing interface having a housing including a therapy cavity adapted to be in fluid communication with the tissue site. In some embodiments, the method may comprise sensing pressure of the fluids at the tissue site using a pressure sensor mounted to the housing in fluid communication with the therapy cavity, sensing humidity of the fluids at the tissue site using a humidity sensor mounted to the housing in fluid communication with the therapy cavity, sensing temperature of the fluids at the tissue site using a temperature sensor mounted to the housing in fluid communication with the therapy cavity, and sensing pH of the fluids at the tissue site using a pH sensor mounted to the housing in fluid communication with the therapy cavity. The method may further comprise logging a first set of property signals from the pressure sensor, the humidity sensor, the temperature sensor, and the pH sensor indicative of the pressure, the humidity, the temperature, and the pH in a processing element mounted to the housing outside the therapy cavity. The method may further comprise purging the fluids from the therapy cavity for sensing the pressure, the humidity, temperature, and the pH of a second sample of the fluids at the tissue site for logging a second set of property signals. The method may further comprise determining flow characteristics of the system by using a processing element mounted to the housing outside the therapy cavity and electrically coupled to the pressure sensor, the humidity sensor, and the temperature sensor for receiving property signals indicative of the pressure, humidity, and temperature. The flow characteristics of the system may include a blockage state condition, and air leak state, a fluid leak state, and/or a desiccation state within the system to provide an alarm indicative of any one of the states based on the property signals.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

The term "tissue site" in this context broadly refers to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective but are instead areas in which it may be desirable to add or promote the growth of additional tissue. For example, negative pressure may be applied to a tissue site to grow additional tissue that may be harvested and transplanted.

Figure 1:
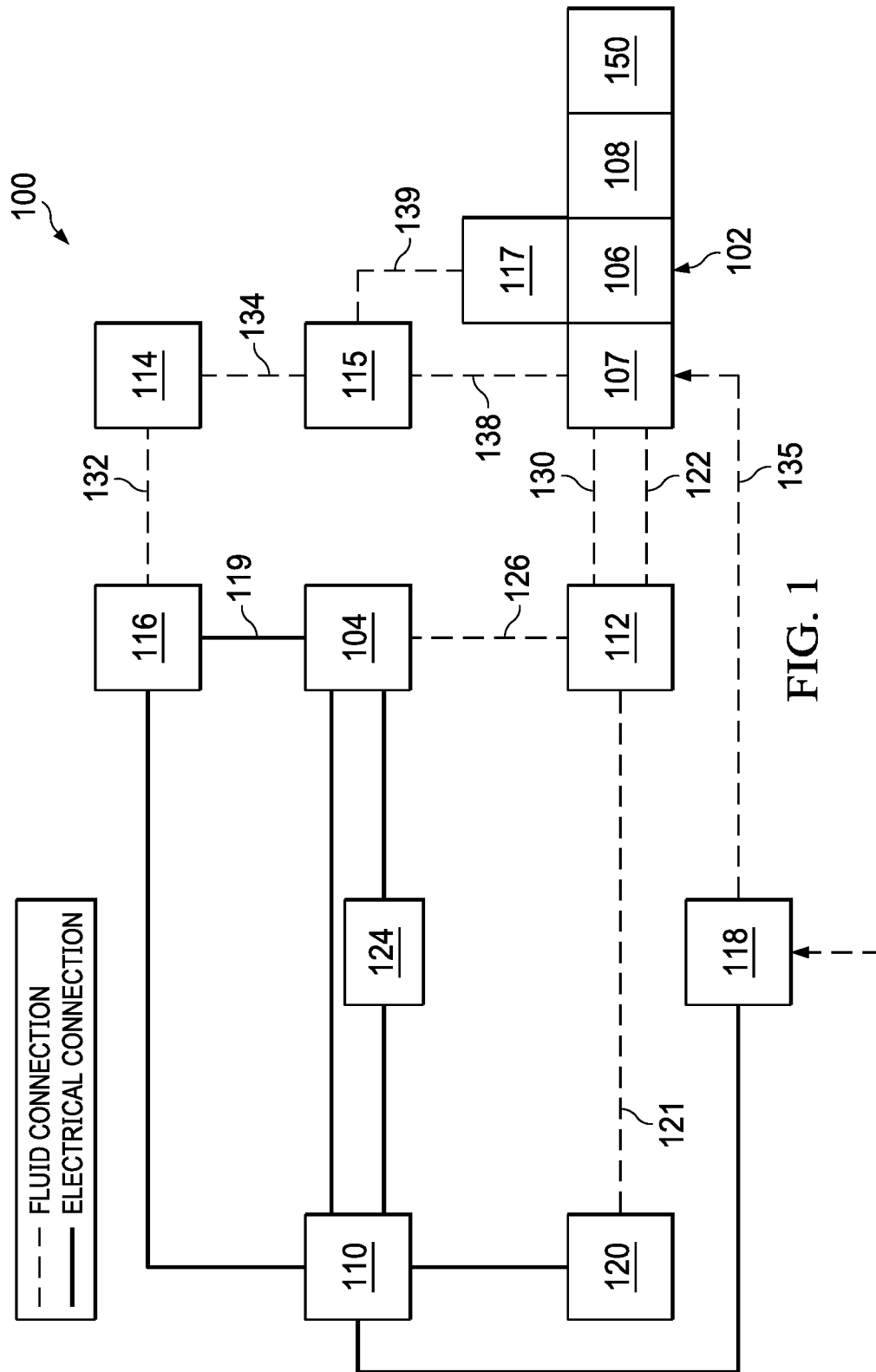
FIG. 1 is a functional block diagram of an example embodiment of a therapy system that can provide negative-pressure and instillation in accordance with this specification.

The present technology also provides negative pressure therapy devices and systems, and methods of treatment using such systems with antimicrobial solutions. FIG. 1 is a simplified functional block diagram of an example embodiment of a therapy system 100 that can provide negative-pressure therapy with instillation of treatment solutions in accordance with this specification. The therapy system 100 may include a negative-pressure supply and may include or be configured to be coupled to a distribution component, such as a dressing. In general, a distribution component may refer to any complementary or ancillary component configured to be fluidly coupled to a negative-pressure supply between a negative-pressure supply and a tissue site. A distribution component is preferably detachable, and may be disposable, reusable, or recyclable. For example, a dressing 102 is illustrative of a distribution component that may be coupled to a negative-pressure source and other components. The therapy system 100 may be packaged as a single, integrated unit such as a therapy system including all of the components shown in FIG. 1 that are fluidly coupled to the dressing 102. The therapy system may be, for example, a V.A.C. Ulta™ System available from Kinetic Concepts, Inc. of San Antonio, Tex.

The dressing 102 may be fluidly coupled to a negative-pressure source 104. A dressing may include a cover, a tissue interface, or both in some embodiments. The dressing 102, for example, may include a cover 106, a dressing interface 107, and a tissue interface 108. A computer or a controller device, such as a controller 110, may also be coupled to the negative-pressure source 104. In some embodiments, the cover 106 may be configured to cover the tissue interface 108 and the tissue site and may be adapted to seal the tissue interface and create a therapeutic environment proximate to a tissue site for maintaining a negative pressure at the tissue site. In some embodiments, the dressing interface 107 may be configured to fluidly couple the negative-pressure source 104 to the therapeutic environment of the dressing. The therapy system 100 may optionally include a fluid container, such as a container 112, fluidly coupled to the dressing 102 and to the negative-pressure source 104.

The therapy system 100 may also include a source of instillation solution, such as a solution source 114. A distribution component may be fluidly coupled to a fluid path between a solution source and a tissue site in some embodiments. For example, an instillation pump 116 may be coupled to the solution source 114, as illustrated in the example embodiment of FIG. 1. The instillation pump 116 may also be fluidly coupled to the negative-pressure source 104 such as, for example, by a fluid conductor 119. In some embodiments, the instillation pump 116 may be directly coupled to the negative-pressure source 104, as illustrated in FIG. 1, but may be indirectly coupled to the negative-pressure source 104 through other distribution components in some embodiments. For example, in some embodiments, the instillation pump 116 may be fluidly coupled to the negative-pressure source 104 through the dressing 102. In some embodiments, the instillation pump 116 and the negative-pressure source 104 may be fluidly coupled to two different locations on the tissue interface 108 by two different dressing interfaces. For example, the negative-pressure source 104 may be fluidly coupled to the dressing interface 107 while the instillation pump 116 may be fluidly to the coupled to dressing interface 107 or a second dressing interface 117. In some other embodiments, the instillation pump 116 and the negative-pressure source 104 may be fluidly coupled to two different tissue interfaces by two different dressing interfaces, one dressing interface for each tissue interface (not shown).

The therapy system 100 also may include sensors to measure operating parameters and provide feedback signals to the controller 110 indicative of the operating parameters properties of fluids extracted from a tissue site. As illustrated in FIG. 1, for example, the therapy system 100 may include a pressure sensor 120, an electric sensor 124, or both, coupled to the controller 110. The pressure sensor 120 may be fluidly coupled or configured to be fluidly coupled to a distribution component such as, for example, the negative-pressure source 104 either directly or indirectly through the container 112. The pressure sensor 120 may be configured to measure pressure being generated by the negative-pressure source 104, i.e., the pump pressure (PP). The electric sensor 124 also may be coupled to the negative-pressure source 104 to measure the pump pressure (PP). In some example embodiments, the electric sensor 124 may be fluidly coupled proximate the output of the output of the negative-pressure source 104 to directly measure the pump pressure (PP). In other example embodiments, the electric sensor 124 may be electrically coupled to the negative-pressure source 104 to measure the changes in the current in order to determine the pump pressure (PP).

Distribution components may be fluidly coupled to each other to provide a distribution system for transferring fluids (i.e., liquid and/or gas). For example, a distribution system may include various combinations of fluid conductors and fittings to facilitate fluid coupling. A fluid conductor generally includes any structure with one or more lumina adapted to convey a fluid between two ends, such as a tube, pipe, hose, or conduit. Typically, a fluid conductor is an elongated, cylindrical structure with some flexibility, but the geometry and rigidity may vary. Some fluid conductors may be molded into or otherwise integrally combined with other components. A fitting can be used to mechanically and fluidly couple components to each other. For example, a fitting may comprise a projection and an aperture. The projection may be configured to be inserted into a fluid conductor so that the aperture aligns with a lumen of the fluid conductor. A valve is a type of fitting that can be used to control fluid flow. For example, a check valve can be used to substantially prevent return flow. A port is another example of a fitting. A port may also have a projection, which may be threaded, flared, tapered, barbed, or otherwise configured to provide a fluid seal when coupled to a component.

In some embodiments, distribution components may also be coupled by virtue of physical proximity, being integral to a single structure, or being formed from the same piece of material. Coupling may also include mechanical, thermal, electrical, or chemical coupling (such as a chemical bond) in some contexts. For example, a tube may mechanically and fluidly couple the dressing 102 to the container 112 in some embodiments. In general, components of the therapy system 100 may be coupled directly or indirectly. For example, the negative-pressure source 104 may be directly coupled to the controller 110, and may be indirectly coupled to the dressing interface 107 through the container 112 by conduit 126 and conduit 130. The pressure sensor 120 may be fluidly coupled to the dressing 102 directly (not shown) or indirectly by conduit 121 and conduit 122. Additionally, the instillation pump 116 may be coupled indirectly to the dressing interface 107 through the solution source 114 and the instillation regulator 115 by fluid conductors 132, 134 and 138. Alternatively, the instillation pump 116 may be coupled indirectly to the second dressing interface 117 through the solution source 114 and the instillation regulator 115 by fluid conductors 132, 134 and 139.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

"Negative pressure" generally refers to a pressure less than a local ambient pressure, such as the ambient pressure in a local environment external to a sealed therapeutic environment provided by the dressing 102. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

A negative-pressure supply, such as the negative-pressure source 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure supply may be housed within or used in conjunction with other components, such as sensors, processing units, alarm indicators, memory, databases, software, display devices, or user interfaces that further facilitate therapy. For example, in some embodiments, the negative-pressure source 104 may be combined with the controller 110 and other components into a therapy unit. A negative-pressure supply may also have one or more supply ports configured to facilitate coupling and de-coupling the negative-pressure supply to one or more distribution components.

The tissue interface 108 can be generally adapted to contact a tissue site. The tissue interface 108 may be partially or fully in contact with the tissue site. If the tissue site is a wound, for example, the tissue interface 108 may partially or completely fill the wound or may be placed over the wound. The tissue interface 108 may take many forms, and may have many sizes, shapes, or thicknesses depending on a variety of factors, such as the type of treatment being implemented or the nature and size of a tissue site. For example, the size and shape of the tissue interface 108 may be adapted to the contours of deep and irregular shaped tissue sites. Moreover, any or all of the surfaces of the tissue interface 108 may have projections or an uneven, course, or jagged profile that can induce strains and stresses on a tissue site, which can promote granulation at the tissue site.

Figure 4:
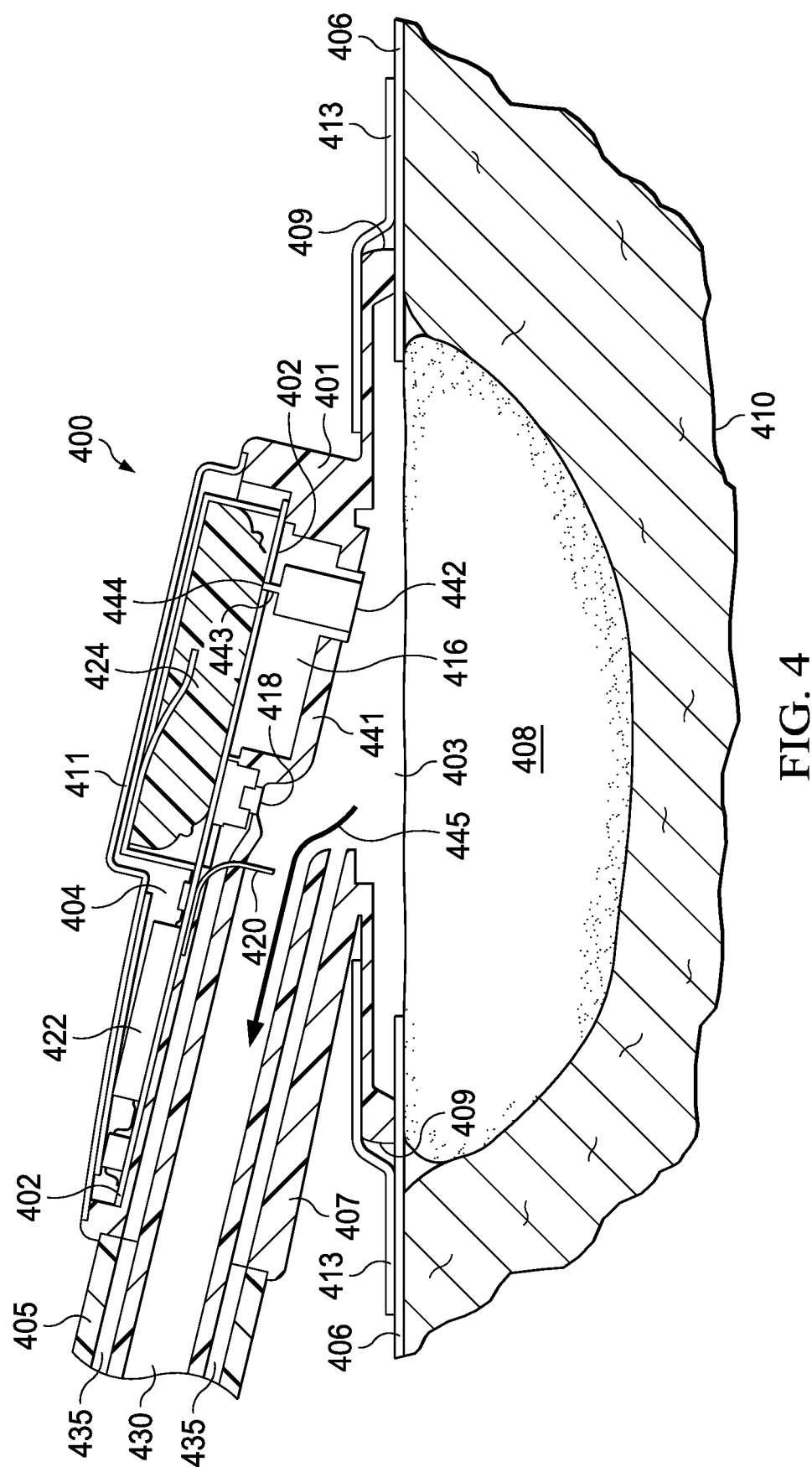
FIG. 4 is a sectional side view of a dressing interface comprising a housing and a wall disposed within the housing and forming a therapy cavity including sensors and a component cavity including electrical devices that may be associated with some example embodiments of the therapy system of FIG. 1.
Figure 5A:
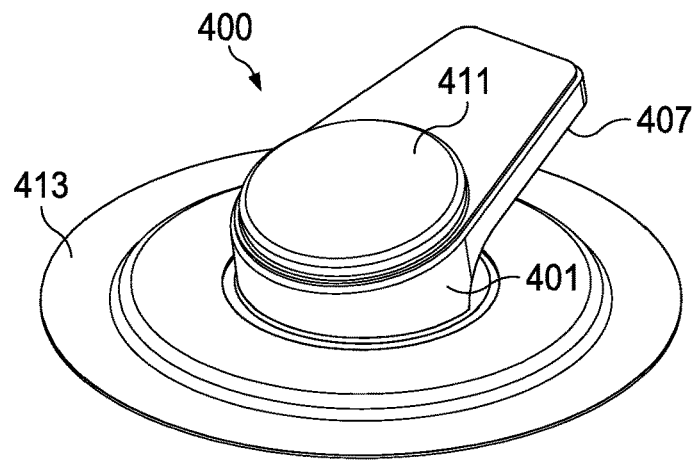
FIG. 5A is a perspective top view of the dressing interface of FIG. 4.
Figure 5B:
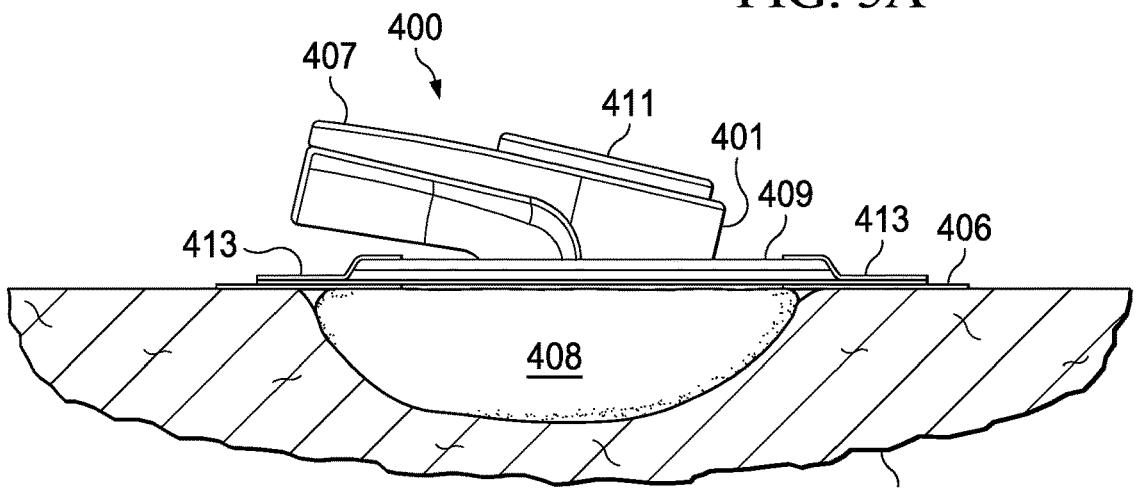
FIG. 5B is a side view of the dressing interface of FIG. 4 disposed on a tissue site.
Figure 5C:
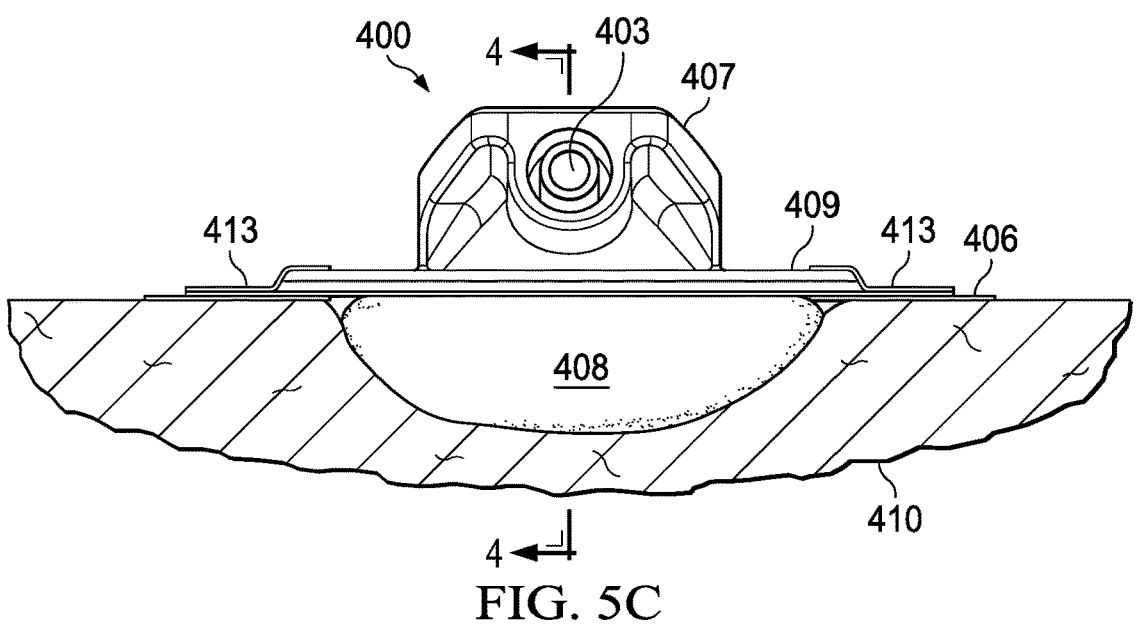
FIG. 5C is an end view of the dressing interface of FIG. 4 disposed on the tissue site.

In some embodiments, the tissue interface 108 may be a manifold such as manifold 408 shown in FIG. 4. A "manifold" in this context generally includes any substance or structure providing a plurality of pathways adapted to collect or distribute fluid across a tissue site under pressure. For example, a manifold may be adapted to receive negative pressure from a source and distribute negative pressure through multiple apertures across a tissue site, which may have the effect of collecting fluid from across a tissue site and drawing the fluid toward the source. In some embodiments, the fluid path may be reversed, or a secondary fluid path may be provided to facilitate delivering fluid across a tissue site.

In some illustrative embodiments, the pathways of a manifold may be interconnected to improve distribution or collection of fluids across a tissue site. In some illustrative embodiments, a manifold may be a porous foam material having interconnected cells or pores. For example, cellular foam, open-cell foam, reticulated foam, porous tissue collections, and other porous material such as gauze or felted mat generally include pores, edges, and/or walls adapted to form interconnected fluid channels. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

The average pore size of a foam manifold may vary according to needs of a prescribed therapy. For example, in some embodiments, the tissue interface 108 may be a foam manifold having pore sizes in a range of 400-600 microns. The tensile strength of the tissue interface 108 may also vary according to needs of a prescribed therapy. For example, the tensile strength of a foam may be increased for instillation of topical treatment solutions. In one non-limiting example, the tissue interface 108 may be an open-cell, reticulated polyurethane foam such as GranuFoam® dressing or VeraFlo® foam, both available from Kinetic Concepts, Inc. of San Antonio, Tex.

The tissue interface 108 may be either hydrophobic or hydrophilic. In an example in which the tissue interface 108 may be hydrophilic, the tissue interface 108 may also wick fluid away from a tissue site, while continuing to distribute negative pressure to the tissue site. The wicking properties of the tissue interface 108 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The tissue interface 108 may further promote granulation at a tissue site when pressure within the sealed therapeutic environment is reduced. For example, any or all of the surfaces of the tissue interface 108 may have an uneven, coarse, or jagged profile that can induce microstrains and stresses at a tissue site if negative pressure is applied through the tissue interface 108.

In some embodiments, the tissue interface 108 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 108 may further serve as a scaffold for new cell-growth, or a scaffold material may be used in conjunction with the tissue interface 108 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 106 may provide a bacterial barrier and protection from physical trauma. The cover 106 may also be constructed from a material that can reduce evaporative losses and provide a fluid seal between two components or two environments, such as between a therapeutic environment and a local external environment. The cover 106 may be, for example, an elastomeric film or membrane that can provide a seal adequate to maintain a negative pressure at a tissue site for a given negative-pressure source. The cover 106 may have a high moisture-vapor transmission rate (MVTR) in some applications. For example, the MVTR may be at least 300 g/m^2 per twenty-four hours in some embodiments. In some example embodiments, the cover 106 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. In some embodiments, the cover may be a drape such as drape 406 shown in FIG. 4.

An attachment device may be used to attach the cover 106 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the cover 106 may be coated with an acrylic adhesive having a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

In some embodiments, the dressing interface 107 may facilitate coupling the negative-pressure source 104 to the dressing 102. The negative pressure provided by the negative-pressure source 104 may be delivered through the conduit 130 to a negative-pressure interface, which may include an elbow portion. In one illustrative embodiment, the negative-pressure interface may be a T.R.A.C.® Pad or Sensa T.R.A.C.® Pad available from KCI of San Antonio, Tex. The negative-pressure interface enables the negative pressure to be delivered through the cover 106 and to the tissue interface 108 and the tissue site. In this illustrative, non-limiting embodiment, the elbow portion may extend through the cover 106 to the tissue interface 108, but numerous arrangements are possible.

A controller, such as the controller 110, may be a microprocessor or computer programmed to operate one or more components of the therapy system 100, such as the negative-pressure source 104. In some embodiments, for example, the controller 110 may be a microcontroller, which generally comprises an integrated circuit containing a processor core and a memory programmed to directly or indirectly control one or more operating parameters of the therapy system 100. Operating parameters may include the power applied to the negative-pressure source 104, the pressure generated by the negative-pressure source 104, or the pressure distributed to the tissue interface 108, for example. The controller 110 is also preferably configured to receive one or more input signals, such as a feedback signal, and programmed to modify one or more operating parameters based on the input signals.

Sensors, such as the pressure sensor 120 or the electric sensor 124, are generally known in the art as any apparatus operable to detect or measure a physical phenomenon or property, and generally provide a signal indicative of the phenomenon or property that is detected or measured. For example, the pressure sensor 120 and the electric sensor 124 may be configured to measure one or more operating parameters of the therapy system 100. In some embodiments, the pressure sensor 120 may be a transducer configured to measure pressure in a pneumatic pathway and convert the measurement to a signal indicative of the pressure measured. In some embodiments, for example, the pressure sensor 120 may be a piezoresistive strain gauge. The electric sensor 124 may optionally measure operating parameters of the negative-pressure source 104, such as the voltage or current, in some embodiments. Preferably, the signals from the pressure sensor 120 and the electric sensor 124 are suitable as an input signal to the controller 110, but some signal conditioning may be appropriate in some embodiments. For example, the signal may need to be filtered or amplified before it can be processed by the controller 110. Typically, the signal is an electrical signal that is transmitted and/or received on by wire or wireless means, but may be represented in other forms, such as an optical signal.

The solution source 114 is representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions. Examples of such other therapeutic solutions that may be suitable for some prescriptions include hypochlorite-based solutions, silver nitrate (0.5%), sulfur-based solutions, biguanides, cationic solutions, and isotonic solutions. In one illustrative embodiment, the solution source 114 may include a storage component for the solution and a separate cassette for holding the storage component and delivering the solution to the tissue site 150, such as a V.A.C. VeraLink™ Cassette available from Kinetic Concepts, Inc. of San Antonio, Tex.

The container 112 may also be representative of a container, canister, pouch, or other storage component, which can be used to collect and manage exudates and other fluids withdrawn from a tissue site. In many environments, a rigid container such as, for example, a container 162, may be preferred or required for collecting, storing, and disposing of fluids. In other environments, fluids may be properly disposed of without rigid container storage, and a re-usable container could reduce waste and costs associated with negative-pressure therapy. In some embodiments, the container 112 may comprise a canister having a collection chamber, a first inlet fluidly coupled to the collection chamber and a first outlet fluidly coupled to the collection chamber and adapted to receive negative pressure from a source of negative pressure. In some embodiments, a first fluid conductor may comprise a first member such as, for example, the conduit 130 fluidly coupled between the first inlet and the tissue interface 108 by the negative-pressure interface described above, and a second member such as, for example, the conduit 126 fluidly coupled between the first outlet and a source of negative pressure whereby the first conductor is adapted to provide negative pressure within the collection chamber to the tissue site.

The therapy system 100 may also comprise a flow regulator such as, for example, a regulator 118 fluidly coupled to a source of ambient air to provide a controlled or managed flow of ambient air to the sealed therapeutic environment provided by the dressing 102 and ultimately the tissue site. In some embodiments, the regulator 118 may control the flow of ambient fluid to purge fluids and exudates from the sealed therapeutic environment. In some embodiments, the regulator 118 may be fluidly coupled by a fluid conductor or vent conduit 135 through the dressing interface 107 to the tissue interface 108. The regulator 118 may be configured to fluidly couple the tissue interface 108 to a source of ambient air as indicated by a dashed arrow. In some embodiments, the regulator 118 may be disposed within the therapy system 100 rather than being proximate to the dressing 102 so that the air flowing through the regulator 118 is less susceptible to accidental blockage during use. In such embodiments, the regulator 118 may be positioned proximate the container 112 and/or proximate a source of ambient air where the regulator 118 is less likely to be blocked during usage.

In operation, the tissue interface 108 may be placed within, over, on, or otherwise proximate a tissue site, such as tissue site 150. The cover 106 may be placed over the tissue interface 108 and sealed to an attachment surface near the tissue site 150. For example, the cover 106 may be sealed to undamaged epidermis peripheral to a tissue site. Thus, the dressing 102 can provide a sealed therapeutic environment proximate to a tissue site, substantially isolated from the external environment, and the negative-pressure source 104 can reduce the pressure in the sealed therapeutic environment. Negative pressure applied across the tissue site through the tissue interface 108 in the sealed therapeutic environment can induce macrostrain and microstrain in the tissue site, as well as remove exudates and other fluids from the tissue site, which can be collected in container 112.

In one embodiment, the controller 110 may receive and process data, such as data related to the pressure distributed to the tissue interface 108 from the pressure sensor 120. The controller 110 may also control the operation of one or more components of therapy system 100 to manage the pressure distributed to the tissue interface 108 for application to the wound at the tissue site 150, which may also be referred to as the wound pressure (WP). In one embodiment, controller 110 may include an input for receiving a desired target pressure (TP) set by a clinician or other user and may be program for processing data relating to the setting and inputting of the target pressure (TP) to be applied to the tissue site 150. In one example embodiment, the target pressure (TP) may be a fixed pressure value determined by a user/caregiver as the reduced pressure target desired for therapy at the tissue site 150 and then provided as input to the controller 110. The user may be a nurse or a doctor or other approved clinician who prescribes the desired negative pressure to which the tissue site 150 should be applied. The desired negative pressure may vary from tissue site to tissue site based on the type of tissue forming the tissue site 150, the type of injury or wound (if any), the medical condition of the patient, and the preference of the attending physician. After selecting the desired target pressure (TP), the negative-pressure source 104 is controlled to achieve the target pressure (TP) desired for application to the tissue site 150.

Figure 2A:
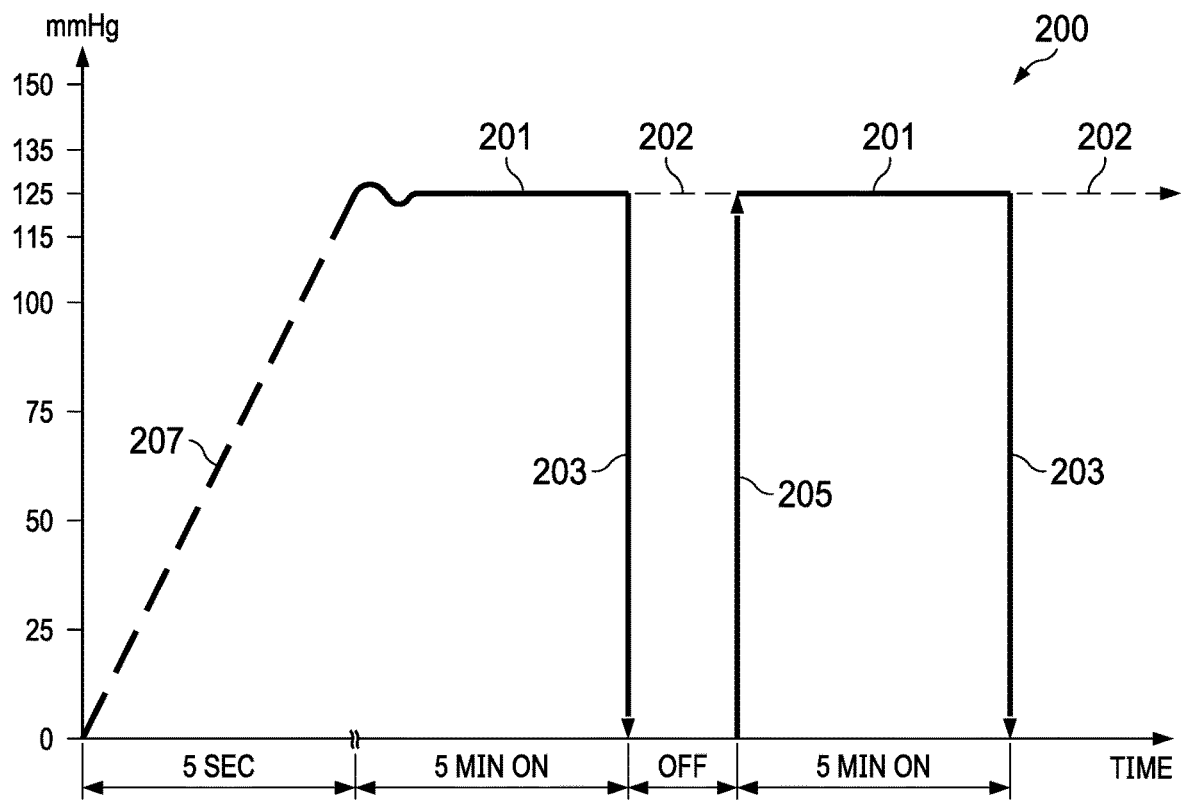
FIG. 2A is a graph illustrating an illustrative embodiment of pressure control modes for the negative-pressure and instillation therapy system of FIG. 1 wherein the x-axis represents time in minutes (min) and/or seconds (sec) and the y-axis represents pressure generated by a pump in Torr (mmHg) that varies with time in a continuous pressure mode and an intermittent pressure mode that may be used for applying negative pressure in the therapy system.

Referring more specifically to FIG. 2A, a graph illustrating an illustrative embodiment of pressure control modes 200 that may be used for the negative-pressure and instillation therapy system of FIG. 1 is shown wherein the x-axis represents time in minutes (min) and/or seconds (sec) and the y-axis represents pressure generated by a pump in Torr (mmHg) that varies with time in a continuous pressure mode and an intermittent pressure mode that may be used for applying negative pressure in the therapy system. The target pressure (TP) may be set by the user in a continuous pressure mode as indicated by solid line 201 and dotted line 202 wherein the wound pressure (WP) is applied to the tissue site 150 until the user deactivates the negative-pressure source 104. The target pressure (TP) may also be set by the user in an intermittent pressure mode as indicated by solid lines 201, 203 and 205 wherein the wound pressure (WP) is cycled between the target pressure (TP) and atmospheric pressure. For example, the target pressure (TP) may be set by the user at a value of 125 mmHg for a specified period of time (e.g., 5 min) followed by the therapy being turned off for a specified period of time (e.g., 2 min) as indicated by the gap between the solid lines 203 and 205 by venting the tissue site 150 to the atmosphere, and then repeating the cycle by turning the therapy back on as indicated by solid line 205 which consequently forms a square wave pattern between the target pressure (TP) level and atmospheric pressure. In some embodiments, the ratio of the "on-time" to the "off-time" or the total "cycle time" may be referred to as a pump duty cycle (PD).

In some example embodiments, the decrease in the wound pressure (WP) at the tissue site 150 from ambient pressure to the target pressure (TP) is not instantaneous, but rather gradual depending on the type of therapy equipment and dressing being used for the particular therapy treatment. For example, the negative-pressure source 104 and the dressing 102 may have an initial rise time as indicated by the dashed line 207 that may vary depending on the type of dressing and therapy equipment being used. For example, the initial rise time for one therapy system may be in the range between about 20-30 mmHg/second or, more specifically, equal to about 25 mmHg/second, and in the range between about 5-10 mmHg/second for another therapy system. When the therapy system 100 is operating in the intermittent mode, the repeating rise time as indicated by the solid line 205 may be a value substantially equal to the initial rise time as indicated by the dashed line 207.

The target pressure may also be a variable target pressure (VTP) controlled or determined by controller 110 that varies in a dynamic pressure mode. For example, the variable target pressure (VTP) may vary between a maximum and minimum pressure value that may be set as an input determined by a user as the range of negative pressures desired for therapy at the tissue site 150. The variable target pressure (VTP) may also be processed and controlled by controller 110 that varies the target pressure (TP) according to a predetermined waveform such as, for example, a sine waveform or a saw-tooth waveform or a triangular waveform, that may be set as an input by a user as the predetermined or time-varying reduced pressures desired for therapy at the tissue site 150.

Figure 2B:
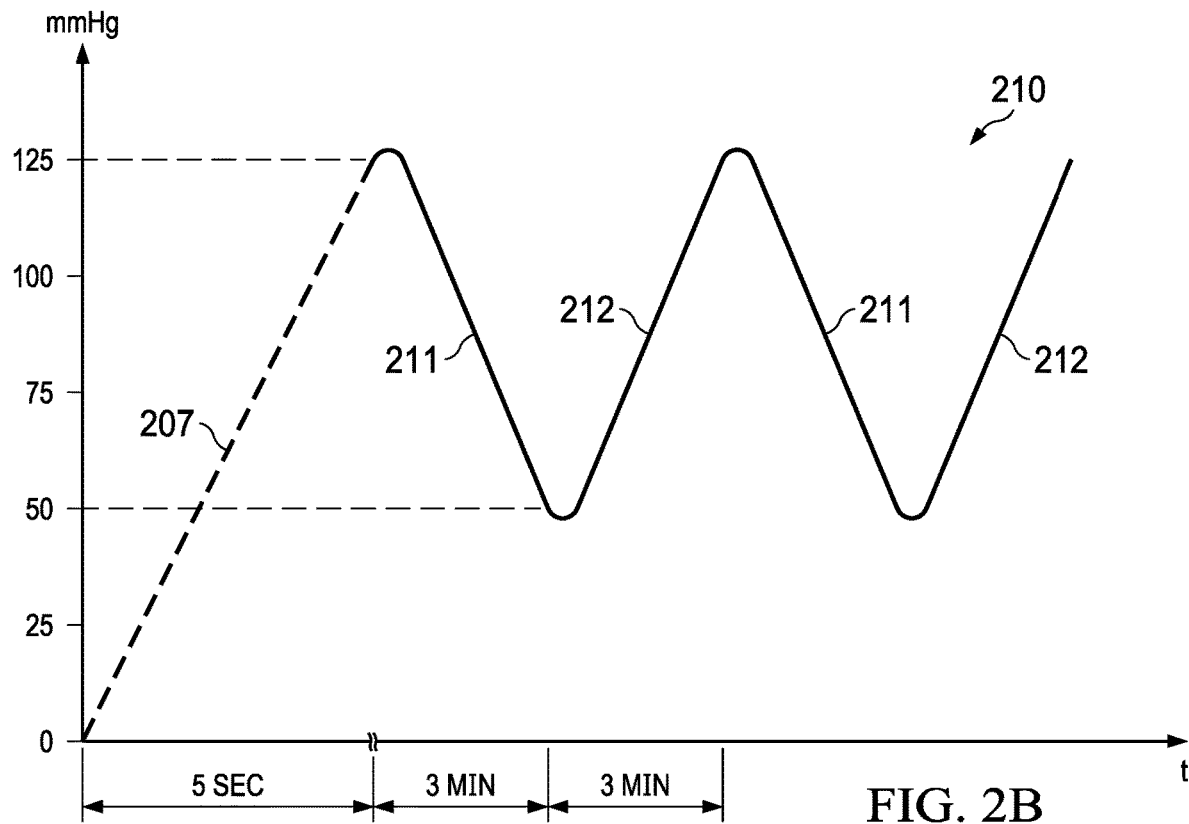
FIG. 2B is a graph illustrating an illustrative embodiment of another pressure control mode for the negative-pressure and instillation therapy system of FIG. 1 wherein the x-axis represents time in minutes (min) and/or seconds (sec) and the y-axis represents pressure generated by a pump in Torr (mmHg) that varies with time in a dynamic pressure mode that may be used for applying negative pressure in the therapy system.

Referring more specifically to FIG. 2B, a graph illustrating an illustrative embodiment of another pressure control mode for the negative-pressure and instillation therapy system of FIG. 1 is shown wherein the x-axis represents time in minutes (min) and/or seconds (sec) and the y-axis represents pressure generated by a pump in Torr (mmHg) that varies with time in a dynamic pressure mode that may be used for applying negative pressure in the therapy system. For example, the variable target pressure (VTP) may be a reduced pressure that provides an effective treatment by applying reduced pressure to tissue site 150 in the form of a triangular waveform varying between a minimum and maximum pressure of 50-125 mmHg with a rise time 212 set at a rate of +25 mmHg/min. and a descent time 211 set at −25 mmHg/min, respectively. In another embodiment of the therapy system 100, the variable target pressure (VTP) may be a reduced pressure that applies reduced pressure to tissue site 150 in the form of a triangular waveform varying between 25-125 mmHg with a rise time 212 set at a rate of +30 mmHg/min and a descent time 211 set at −30 mmHg/min. Again, the type of system and tissue site determines the type of reduced pressure therapy to be used.

Figure 3:
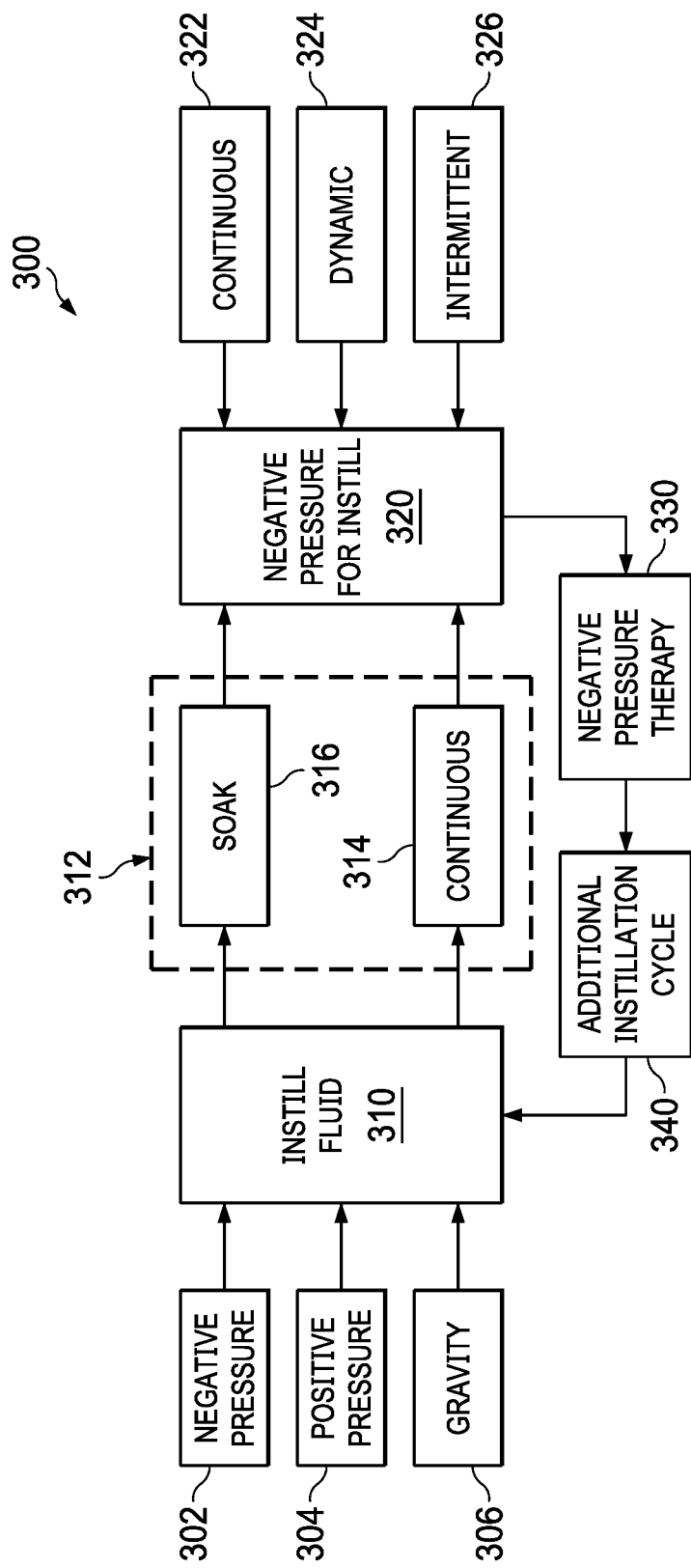
FIG. 3 is a schematic block diagram showing an illustrative embodiment of a therapy method for providing negative-pressure and instillation therapy for delivering treatment solutions to a dressing at a tissue site.

FIG. 3 is a flow chart illustrating an illustrative embodiment of a therapy method 300 that may be used for providing negative-pressure and instillation therapy for delivering an antimicrobial solution or other treatment solution to a dressing at a tissue site. In one embodiment, the controller 110 receives and processes data, such as data related to fluids provided to the tissue interface. Such data may include the type of instillation solution prescribed by a clinician, the volume of fluid or solution to be instilled to the tissue site ("fill volume"), and the amount of time needed to soak the tissue interface ("soak time") before applying a negative pressure to the tissue site. The fill volume may be, for example, between 10 and 500 mL, and the soak time may be between one second to 30 minutes. The controller 110 may also control the operation of one or more components of the therapy system 100 to manage the fluids distributed from the solution source 114 for instillation to the tissue site 150 for application to the wound as described in more detail above. In one embodiment, fluid may be instilled to the tissue site 150 by applying a negative pressure from the negative-pressure source 104 to reduce the pressure at the tissue site 150 to draw the instillation fluid into the dressing 102 as indicated at 302. In another embodiment, fluid may be instilled to the tissue site 150 by applying a positive pressure from the negative-pressure source 104 (not shown) or the instillation pump 116 to force the instillation fluid from the solution source 114 to the tissue interface 108 as indicated at 304. In yet another embodiment, fluid may be instilled to the tissue site 150 by elevating the solution source 114 to height sufficient to force the instillation fluid into the tissue interface 108 by the force of gravity as indicated at 306. Thus, the therapy method 300 includes instilling fluid into the tissue interface 108 by either drawing or forcing the fluid into the tissue interface 108 as indicated at 310.

The therapy method 300 may control the fluid dynamics of applying the fluid solution to the tissue interface 108 at 312 by providing a continuous flow of fluid at 314 or an intermittent flow of fluid for soaking the tissue interface 108 at 316. The therapy method 300 may include the application of negative pressure to the tissue interface 108 to provide either the continuous flow or intermittent soaking flow of fluid at 320. The application of negative pressure may be implemented to provide a continuous pressure mode of operation at 322 as described above to achieve a continuous flow rate of instillation fluid through the tissue interface 108 or a dynamic pressure mode of operation at 324 as described above to vary the flow rate of instillation fluid through the tissue interface 108. Alternatively, the application of negative pressure may be implemented to provide an intermittent mode of operation at 326 as described above to allow instillation fluid to soak into the tissue interface 108 as described above. In the intermittent mode, a specific fill volume and the soak time may be provided depending, for example, on the type of wound being treated and the type of dressing 102 being utilized to treat the wound. After or during instillation of fluid into the tissue interface 108 has been completed, the therapy method 300 may begin may be utilized using any one of the three modes of operation at 330 as described above. The controller 110 may be utilized to select any one of these three modes of operation and the duration of the negative pressure therapy as described above before commencing another instillation cycle at 340 by instilling more fluid at 310.

As discussed above, the tissue site 150 may include, without limitation, any irregularity with a tissue, such as an open wound, surgical incision, or diseased tissue. The therapy system 100 is presented in the context of a tissue site that includes a wound that may extend through the epidermis and the dermis and may reach into the hypodermis or subcutaneous tissue. The therapy system 100 may be used to treat a wound of any depth, as well as many different types of wounds including open wounds, incisions, or other tissue sites. The tissue site 150 may be the bodily tissue of any human, animal, or other organism, including bone tissue, adipose tissue, muscle tissue, dermal tissue, vascular tissue, connective tissue, cartilage, tendons, ligaments, or any other tissue. Treatment of the tissue site 150 may include removal of fluids originating from the tissue site 150, such as exudates or ascites, or fluids instilled into the dressing to cleanse or treat the tissue site 150, such as antimicrobial solutions.

As indicated above, the therapy system 100 may be packaged as a single, integrated unit such as a therapy system including all of the components shown in FIG. 1 that are fluidly coupled to the dressing 102. In some embodiments, an integrated therapy unit may include the negative-pressure source 104, the controller 110, the pressure sensor 120, and the container 112 which may be fluidly coupled to the dressing interface 107. In this therapy unit, the negative-pressure source 104 is indirectly coupled to the dressing interface 107 through the container 112 by conduit 126 and conduit 130, and the pressure sensor 120 is indirectly coupled to the dressing interface 107 by conduit 121 and conduit 122 as described above. In some embodiments, the negative pressure conduit 130 and the pressure sensing conduit 122 may be combined in a single fluid conductor that can be, for example, a multi-lumen tubing comprising a central primary lumen that functions as the negative pressure conduit 130 for delivering negative pressure to the dressing interface 107 and several peripheral auxiliary lumens that function as the pressure sensing conduit 122 for sensing the pressure that the dressing interface 107 delivers to the tissue interface 108. In this type of therapy unit wherein the pressure sensor 120 is removed from and indirectly coupled to the dressing interface 107, the negative pressure measured by the pressure sensor 120 may be different from the wound pressure (WP) actually being applied to the tissue site 150. Such pressure differences must be approximated in order to adjust the negative-pressure source 104 to deliver the pump pressure (PP) necessary to provide the desired or target pressure (TP) to the tissue interface 108. Moreover, such pressure differences and predictability may be exacerbated by viscous fluids such as exudates being produced by the tissue site or utilizing a single therapy device including a pressure sensor to deliver negative pressure to multiple tissue sites on a single patient.

What is needed is a pressure sensor that is integrated within the dressing interface 107 so that the pressure sensor is proximate the tissue interface 108 when disposed on the tissue site in order to provide a more accurate reading of the wound pressure (WP) being provided within the therapy environment of the dressing 102. The integrated pressure sensor may be used with or without the remote pressure sensor 120 that is indirectly coupled to the dressing interface 107. In some example embodiments, the dressing interface 107 may comprise a housing having a therapy cavity that opens to the tissue site when positioned thereon. The integrated pressure sensor may have a sensing portion disposed within the therapy cavity along with other sensors including, for example, a temperature sensor, a humidity sensor, and a pH sensor. The sensors may be electrically coupled to the controller 110 outside the therapy cavity to provide data indicative of the pressure, temperature, humidity, and acidity properties within the therapeutic space of the therapy cavity. The sensors may be electrically coupled to the controller 110, for example, by wireless means. Systems, apparatuses, and methods described herein provide the advantage of more accurate measurements of these properties, as well as other significant advantages described below in more detail.

As indicated above, the dressing 102 may include the cover 106, the dressing interface 107, and the tissue interface 108. Referring now to FIGS. 4, 5A, 5B, 5C, 6A, 6B, and 7, a first dressing is shown comprising a dressing interface 400, a cover or drape 406, and a tissue interface or manifold 408 disposed adjacent a tissue site 410, all of which may be functionally similar in part to the dressing interface 107, the cover 106, and the tissue interface 108, respectively, as described above. In one example embodiment, the dressing interface 400 may comprise a housing 401 and a wall 402 disposed within the housing 401 wherein the wall 402 forms a recessed space or a therapy cavity 403 that opens to the manifold 408 when disposed at the tissue site 410 and a component cavity 404 opening away from the tissue site 410 of the upper portion of the dressing interface 400. In some embodiments, sensing portions of various sensors may be disposed within the therapy cavity 403, and electrical devices associated with the sensors may be disposed within the component cavity 404 and electrically coupled to the sensing portions through the wall 402. Electrical devices disposed within the component cavity 404 may include components associated with some example embodiments of the therapy system of FIG. 1. Although the dressing interface 400 and the therapy cavity 403 are functionally similar to the dressing interface 107 as described above, the dressing interface 400 further comprises the wall 402, the sensors, and the associated electrical devices described below in more detail. In some embodiments, the housing 401 may further comprise a neck portion or neck 407 fluidly coupled to a conduit 405. In some embodiments, the housing 401 may further comprise a flange portion or flange 409 having flow channels (see FIG. 8) configured to be fluidly coupled to the therapy cavity 403 when disposed on the manifold 408.

In some example embodiments, the neck 407 of the housing 401 may include portions of both the therapy cavity 403 and the component cavity 404. That portion of the neck 407 extending into the therapy cavity 403 is fluidly coupled to the conduit 405, while the portion extending into the component cavity 404 may contain some of the electrical devices. In some example embodiments, the conduit 405 may comprise a primary lumen 430 and auxiliary lumens 435 fluidly coupled by the neck 407 of the housing 401 to the therapy cavity 403. The primary lumen 430 is similar to the negative pressure conduit 130 that may be coupled indirectly to the negative-pressure source 104. The auxiliary lumens 435 are collectively similar to the vent conduit 135 that may be fluidly coupled to the regulator 118 for purging fluids from the therapy cavity 403.

In some embodiments, the component cavity 404 containing the electrical devices may be open to the ambient environment such that the electrical devices are exposed to the ambient environment. In other example embodiments, the component cavity 404 may be closed by a cover such as, for example, a cap 411 to protect the electrical devices. In still other embodiments, the component cavity 404 covered by the cap 411 may still be vented to the ambient environment to provide cooling to the electrical devices and a source of ambient pressure for a pressure sensor disposed in the therapy cavity 403 as described in more detail below. The first dressing may further comprise a drape ring 413 covering the circumference of the flange 409 and the adjacent portion of the drape 406 to seal the therapy cavity 403 of the housing 401 over the manifold 408 and the tissue site 410. In some embodiments, the drape ring 413 may comprise a polyurethane film including and an attachment device such as, for example, an acrylic, polyurethane gel, silicone, or hybrid combination of the foregoing adhesives (not shown) to attach the drape ring 413 to the flange 409 and the drape 406. The attachment device of drape ring 413 may be a single element of silicon or hydrocolloid with the adhesive on each side that functions as a gasket between the drape 406 and the flange 409. In some embodiments, the drape ring 413 may be similar to the cover 106 and/or the attachment device described above in more detail.

In some embodiments, a pressure sensor 416, a temperature and humidity sensor 418, and a pH sensor 420 (collectively referred to below as "the sensors") may be disposed in the housing 401 with each one having a sensing portion extending into the therapy cavity 403 of the housing 401 and associated electronics disposed within the component cavity 404. The housing 401 may include other types of sensors, or combinations of the foregoing sensors, such as, for example, oxygen sensors. In some example embodiments, the sensors may be coupled to or mounted on the wall 402 and electrically coupled to electrical components and circuits disposed within the component cavity 404 by electrical conductors extending through the wall 402. In some preferred embodiments, the electrical conductors extend through pathways in the wall 402 while keeping the therapy cavity 403 electrically and pneumatically isolated from the component cavity 404. For example, the wall 402 may comprise a circuit board 432 on which the electrical circuits and/or components may be printed or mounted. In some other examples, the circuit board 432 may be the wall 402 that covers an opening between the therapy cavity 403 and the component cavity 404, and pneumatically seals the therapy cavity 403 from the component cavity 404 when seated over the opening.

In some embodiments, the electrical circuits and/or components associated with the sensors that are mounted on the circuit board 432 within the component cavity 404 may be electrically coupled to the controller 110 to interface with the rest of the therapy system 100 as described above. In some embodiments, for example, the electrical circuits and/or components may be electrically coupled to the controller 110 by a conductor that may be a component of the conduit 405. In some other preferred embodiments, a communications module 422 may be disposed in the component cavity 404 of the housing 401 and mounted on the circuit board 432 within the component cavity 404. Using a wireless communications module 422 has the advantage of eliminating an electrical conductor between the dressing interface 400 and the integrated portion of the therapy system 100 that may become entangled with the conduit 405 when in use during therapy treatments. For example, the electrical circuits and/or components associated with the sensors along with the terminal portion of the sensors may be electrically coupled to the controller 110 by wireless means such as an integrated device implementing Bluetooth® Low Energy wireless technology. More specifically, the communications module 422 may be a Bluetooth® Low Energy system-on-chip that includes a microprocessor (an example of the microprocessors referred to hereinafter) such as the nRF51822 chip available from Nordic Semiconductor. The wireless communications module 422 may be implemented with other wireless technologies suitable for use in the medical environment.

Figure 6A:
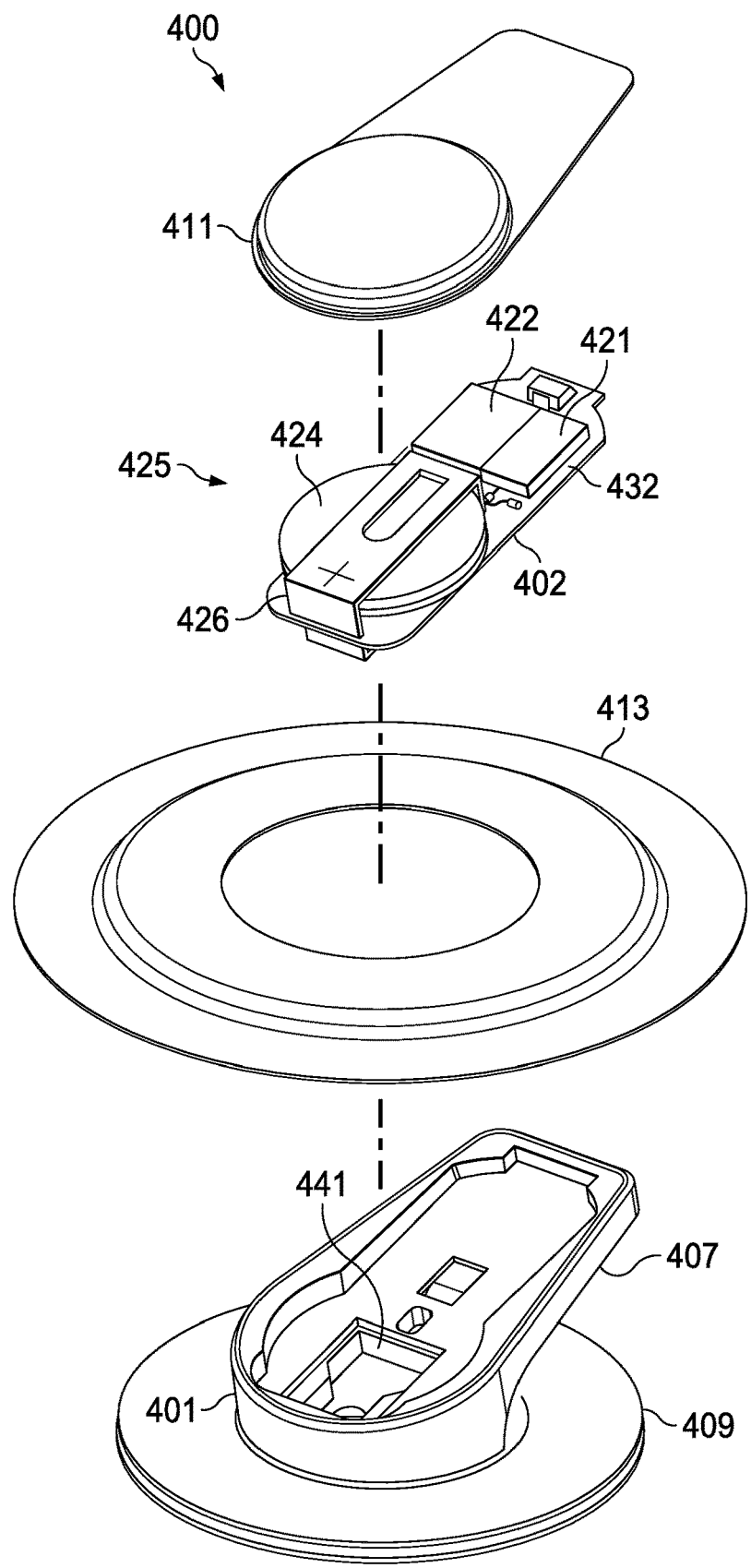
FIG. 6A is an assembly view of the dressing interface of FIG. 4 comprising components of the housing and a first example embodiment of a sensor assembly including the wall, the sensors, and the electrical devices.
Figure 6B:
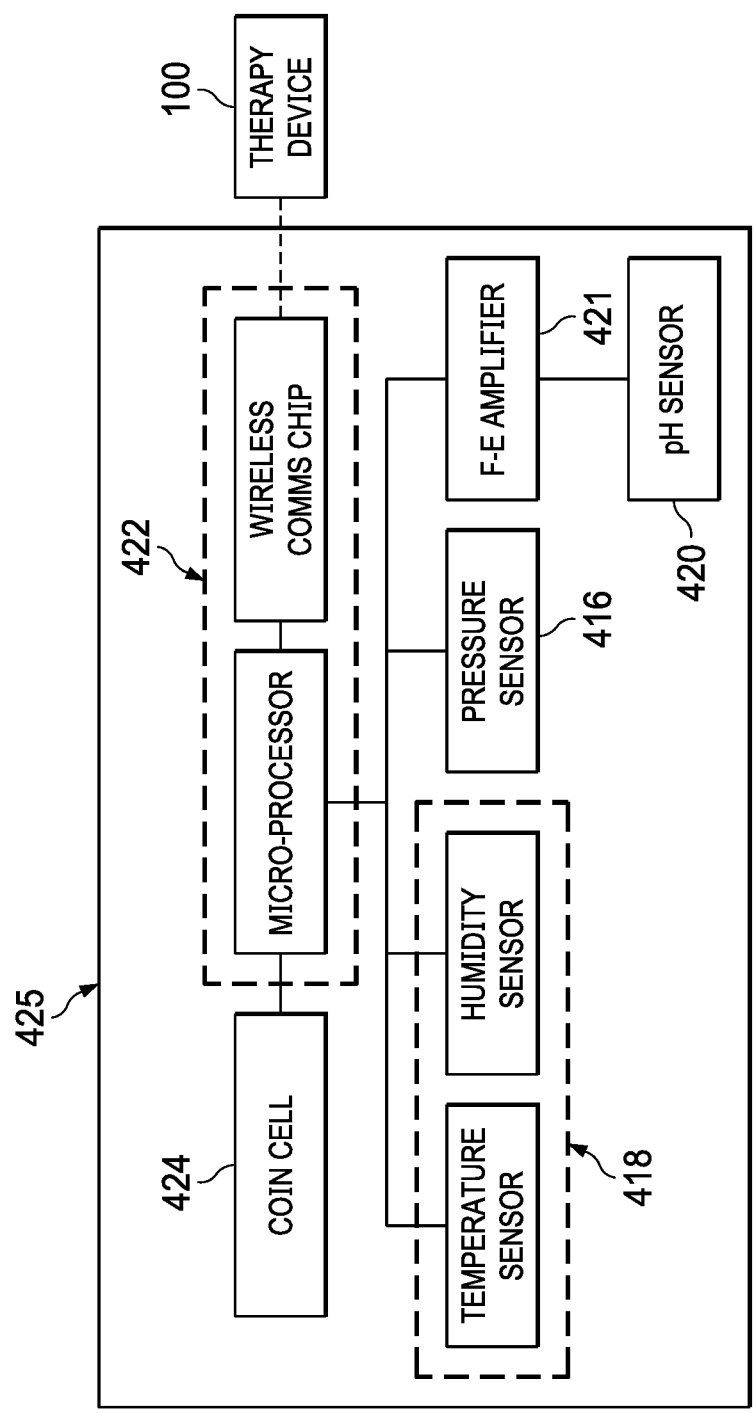
FIG. 6B is a system block diagram of the sensors and electrical devices comprising the sensor assembly of FIG. 6A.
Figure 7A:
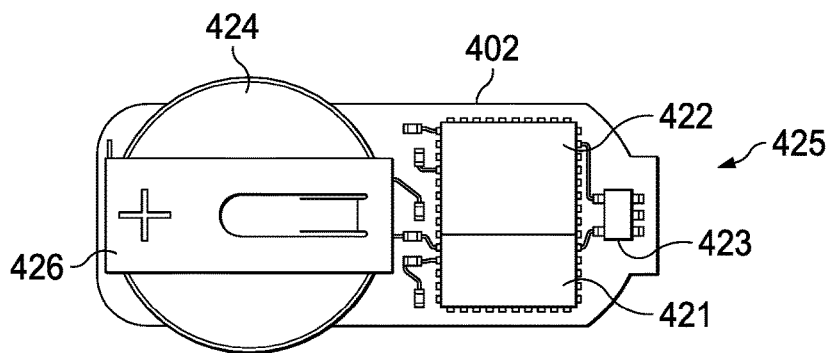
FIGS. 7A, 7B and 7C are a top view, side view, and bottom view, respectively, of the sensor assembly of FIG. 6.
Figure 7B:
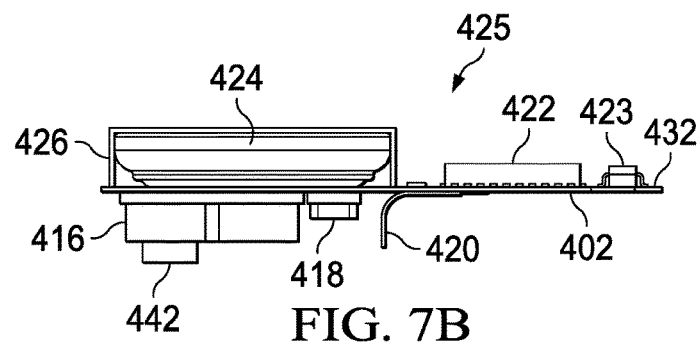
Figure 7C:
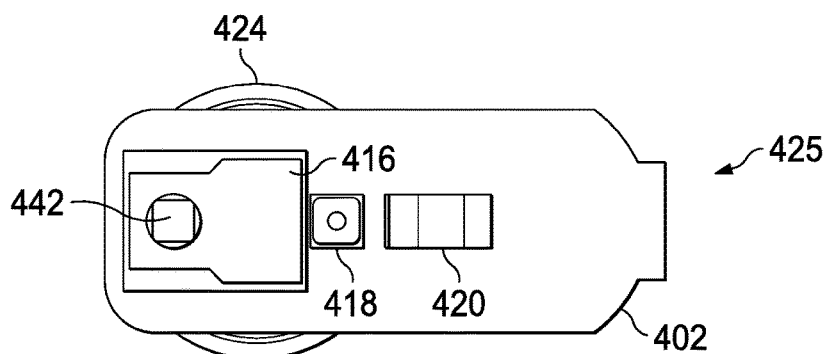
Figure 7D:
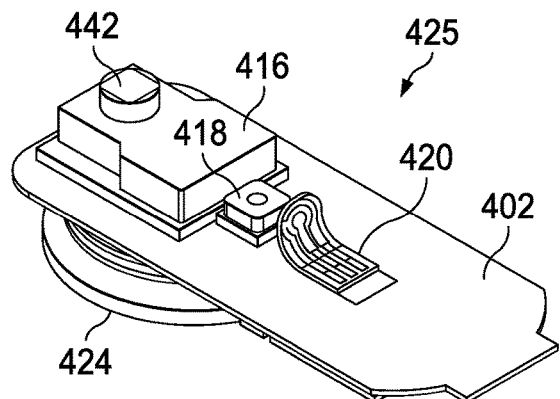
FIG. 7D is a perspective top view of the sensor assembly of the sensor assembly of FIG. 6 including one example embodiment of a pH sensor.

In some embodiments, a voltage regulator 423 for signal conditioning and a power source 424 may be disposed within the component cavity 404 of the housing 401, mounted on the circuit board 432. The power supply 424 may be secured to the circuit board 432 by a bracket 426. The power source 424 may be, for example, a battery that may be a coin battery having a low-profile that provides a 3-volt source for the communications module 422 and the other electronic components within the component cavity 404 associated with the sensors. In some example embodiments, the sensors, the electrical circuits and/or components associated with the sensors, the wall 402 and/or the circuit board 432, the communications module 422, and the power source 424 may be integrated into a single package and referred to hereinafter as a sensor assembly 425 as shown in FIG. 6B. In some preferred embodiments, the wall 402 of the sensor assembly 425 may be the circuit board 432 itself as described above that provides a seal between tissue site 410 and the atmosphere when positioned over the opening between the therapy cavity 403 and the component cavity 404 of the housing 401 and functions as the wall 402 within the housing 401 that forms the therapy cavity 403.

Figure 8A:
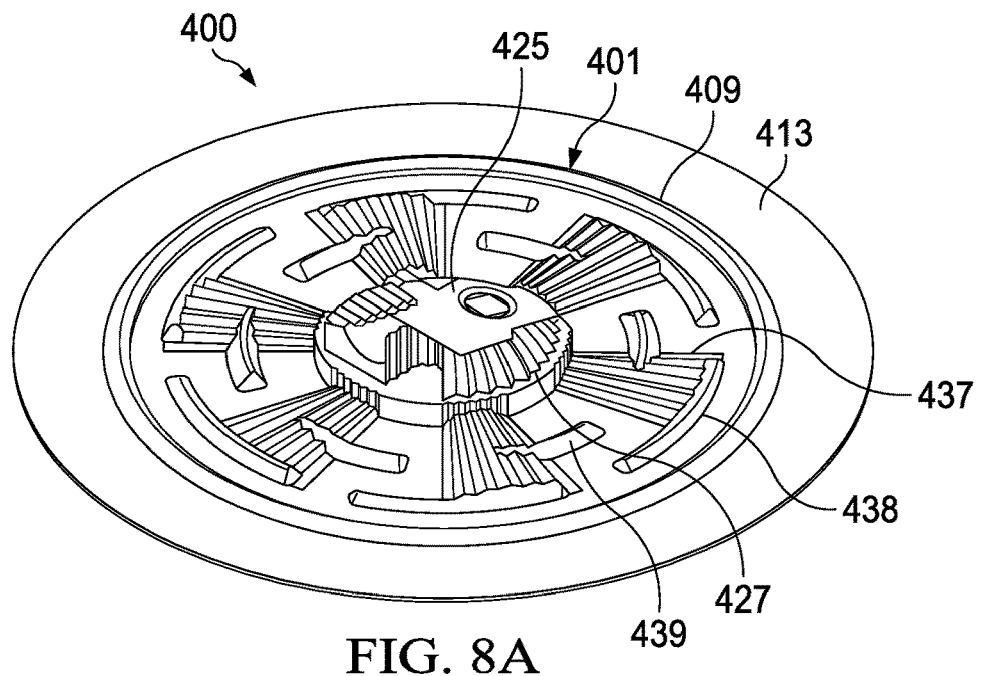
FIG. 8A is a perspective bottom view of the dressing interface of FIG. 4.
Figure 8B:
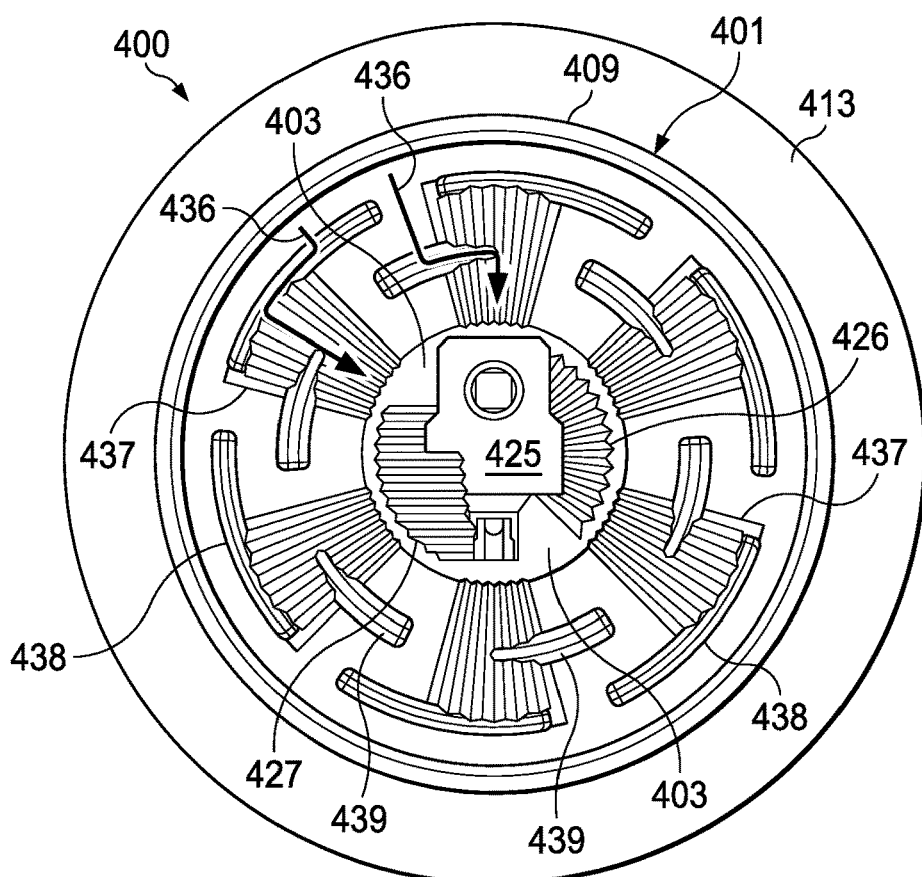
FIG. 8B is a bottom view of the dressing interface of FIG. 4.

Referring now to FIGS. 8A and 8B, a perspective view and a bottom view, respectively, of a bottom surface of the flange 409 facing the manifold 408 is shown. In some embodiments, the bottom surface may comprise features or channels to direct the flow of liquids and/or exudates away from the sensors out of the therapy cavity 403 into the primary lumen 430 when negative pressure is being applied to the therapy cavity 403. In some embodiments, these channels may be molded into the bottom surface of the flange 409 to form a plurality of serrated guide channels 437, perimeter collection channels 438, and intermediate collection channels 439. The serrated guide channels 437 may be positioned and oriented in groups on bottom surface to directly capture and channel at least half of the liquids being drawn into the therapy cavity 403 with the groups of serrated guide channels 437, and indirectly channel a major portion of the balance of the liquids being drawn into the therapy cavity 403 between the groups of serrated guide channels 437. In addition, perimeter collection channels 438 and intermediate collection channels 439 redirect the flow of liquids that are being drawn in between the groups of radially-oriented serrated guide channels 437 into the guide channels 437. An example of this redirected flow is illustrated by bolded flow arrows 436. In some example embodiments, a portion of the housing 401 within the therapy cavity 403 may comprise a second set of serrated guide channels 427 spaced apart and radially-oriented to funnel liquids being drawn into the therapy cavity 403 from the flange 409 into the primary lumen 430. In other example embodiments of the bottom surface of the flange 409 and that portion of the housing 401 within the therapy cavity 403, the channels may be arranged in different patterns.

As indicated above, the sensor assembly 425 may comprise a pressure sensor 416, a humidity sensor 418, a temperature sensor as a component of either the pressure sensor 416 or the humidity sensor 418, and a pH sensor 420. Each of the sensors may comprise a sensing portion extending into the therapy cavity 403 of the housing 401 and a terminal portion electrically coupled to the electrical circuits and/or components within the component cavity 404. Referring more specifically to FIGS. 4, 6A, 6B, and 7A-7D, the housing 401 may comprise a sensor bracket 441 that may be a molded portion of the housing 401 within the therapy cavity 403 in some embodiments. The sensor bracket 441 may be structured to house and secure the pressure sensor 416 on the circuit board 432 within the therapy cavity 403 of the sensor assembly 425 that provides a seal between tissue site 410 and the atmosphere as described above. In some embodiments, the pressure sensor 416 may be a differential gauge comprising a sensing portion 442 and a terminal portion or vent 443. The vent 443 of the pressure sensor 416 may be fluidly coupled through the circuit board 432 to the component cavity 404 and the atmosphere by a vent hole 444 extending through the circuit board 432. Because the component cavity 404 is vented to the ambient environment, the vent 443 of the pressure sensor 416 is able to measure the wound pressure (WP) with reference to the ambient pressure. The sensing portion 442 of the pressure sensor 416 may be positioned in close proximity to the manifold 408 to optimize fluid coupling and accurately measure the wound pressure (WP) at the tissue site 410. In some embodiments, the pressure sensor 416 may be a piezo-resistive pressure sensor having a pressure sensing element covered by a dielectric gel such as, for example, a Model 1620 pressure sensor available from TE Connectivity. The dielectric gel provides electrical and fluid isolation from the blood and wound exudates in order to protect the sensing element from corrosion or other degradation. This allows the pressure sensor 416 to measure the wound pressure (WP) directly within the therapy cavity 403 of the housing 401 proximate to the manifold 408 as opposed to measuring the wound pressure (WP) from a remote location. In some embodiments, the pressure sensor 416 may be a gauge that measures the absolute pressure that does not need to be vented.

In some embodiments, the pressure sensor 416 also may comprise a temperature sensor for measuring the temperature at the tissue site 410. In other embodiments, the humidity sensor 418 may comprise a temperature sensor for measuring the temperature at the tissue site 410. The sensor bracket 441 also may be structured to support the humidity sensor 418 on the circuit board 432 of the sensor assembly 425. In some embodiments, the humidity sensor 418 may comprise a sensing portion that is electrically coupled through the circuit board 432 to a microprocessor mounted on the other side of the circuit board 432 within the component cavity 404. The sensing portion of the humidity sensor 418 may be fluidly coupled to the space within the therapy cavity 403 that includes a fluid pathway 445 extending from the therapy cavity 403 into the primary lumen 430 of the conduit 405 as indicated by the bold arrow to sense both the humidity and the temperature. The sensing portion of the humidity sensor 418 may be positioned within the fluid pathway 445 to limit direct contact with bodily fluids being drawn into the primary lumen 430 from the tissue site 410. In some embodiments, the space within the therapy cavity 403 adjacent the sensing portion of the humidity sensor 418 may be purged by venting that space through the auxiliary lumens 435 as described in more detail below. As indicated above, the humidity sensor 418 may further comprise a temperature sensor (not shown) as the location within the fluid pathway 445 is well-suited to achieve accurate readings of the temperature of the fluids. In some embodiments, the humidity sensor 418 that comprises a temperature sensor may be a single integrated device such as, for example, Model HTU28 humidity sensor also available from TE Connectivity.

Figure 9A:
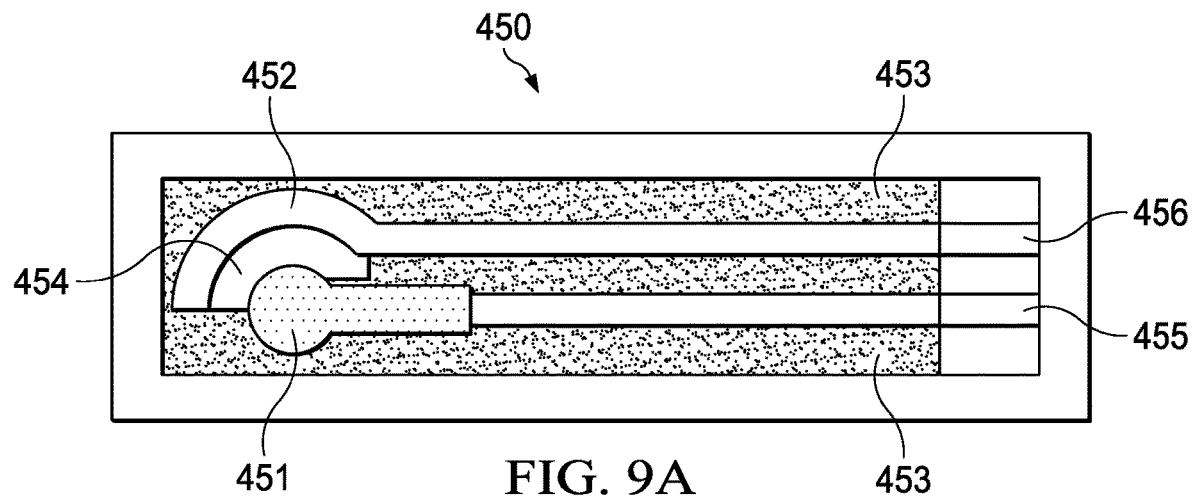
FIG. 9A is a top view of a first embodiment of a pH sensor that may be used with the sensor assembly of FIG. 8D.
Figure 9B:
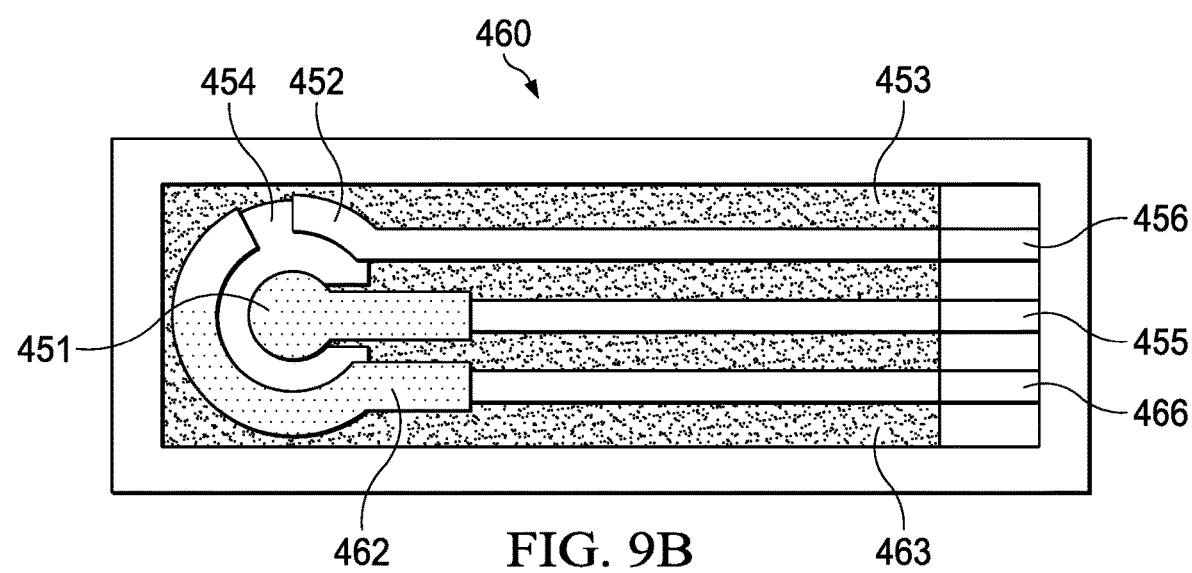
FIG. 9B is a top view of a second embodiment of a pH sensor that may be used with the sensor assembly of FIG. 8D.

Referring now to FIGS. 9A and 9B, the pH sensor 420 may comprise a sensing portion disposed within the therapy cavity 403 that is electrically coupled through the circuit board 432 to a front-end amplifier 421 mounted on the other side of the circuit board 432 within the component cavity 404. The front-end amplifier 421 comprises analog signal conditioning circuitry that includes sensitive analog amplifiers such as, for example, operational amplifiers, filters, and application-specific integrated circuits. The front-end amplifier 421 measures minute voltage potential changes provided by the sensing portions to provide an output signal indicative of the pH of the fluids. The sensing portion of the pH sensor 420 may be fluidly coupled to the space within the therapy cavity 403 by being positioned in the fluid pathway 445 that extends into the primary lumen 430 as described above to sense the pH changes. The sensing portion of the pH sensor 420 may be formed and positioned within the fluid pathway 445 so that the sensing portion directly contacts the wound fluid without contacting the wound itself so that the sensing portion of the pH sensor 420 does not interfere with the wound healing process. In some embodiments, the space within the therapy cavity 403 adjacent the sensing portion of the pH sensor 420 also may be purged by venting that space through the auxiliary lumens 435 as described in more detail below. In some embodiments, the pH sensor 420 may be, for example, pH sensor 450 shown in FIG. 9A that comprises a pair of printed medical electrodes including a working electrode 451 and a reference electrode 452. In some embodiments, the working electrode 451 may have a node being substantially circular in shape at one end and having a terminal portion at the other end, and the reference electrode 452 may have a node being substantially semicircular in shape and disposed around the node of the working electrode 451.

In some example embodiments, the working electrode 451 may comprise a material selected from a group including graphene oxide ink, conductive carbon, carbon nanotube inks, silver, nano-silver, silver chloride ink, gold, nano-gold, gold-based ink, metal oxides, conductive polymers, or a combination thereof. This working electrode 451 further comprise a coating or film applied over the material wherein such coating or film may be selected from a group including metal oxides such as, for example, tungsten, platinum, iridium, ruthenium, and antimony oxides, or a group of conductive polymers such as polyaniline and others so that the conductivity of the working electrode 451 changes based on changes in hydrogen ion concentration of the fluids being measured or sampled. In some example embodiments, the reference electrode 452 may comprise a material selected from a group including silver, nano-silver, silver chloride ink, or a combination thereof. The pH sensor 450 may further comprise a coating 453 covering the electrodes that insulates and isolates the working electrode 451 from the reference electrode 452 and the wound fluid, except for an electrical coupling space 454 between the nodes of the working electrode 451 and the reference electrode 452. The coating 453 does not cover the terminal portions of the working electrode 451 and the reference electrode 452 to form terminals 455 and 456, respectively, adapted to be electrically coupled to the front-end amplifier 421.

In some example embodiments, the terminal portion of the working electrode 451 and the reference electrode 452 may extend through the circuit board 432 and electrically coupled to the front-end amplifier 421 of the pH sensor 450. As indicated above, the front-end amplifier 421 of the pH sensor 450 measures minute potential changes between the working electrode 451 and the reference electrode 452 that result from a change in hydrogen ion concentration of the wound fluid as the pH of the wound fluid changes. The front-end amplifier 421 may be, for example, an extremely accurate voltmeter that measures the voltage potential between the working electrode 451 and the reference electrode 452. The front-end amplifier 421 may be for example a high impedance analog front-end (AFE) device such as the LMP7721 and LMP91200 chips that are available from manufacturers such as Texas Instruments and the AD7793 and AD8603 chips that are available from manufacturers such as Analog Devices.

In some other embodiments, the pH sensor 420 may include a third electrode such as, for example, pH sensor 460 shown in FIG. 9B that comprises a third electrode or a counter electrode 462 in addition to the working electrode 451 and the reference electrode 452 of the pH sensor 450. The counter electrode 462 also comprises a node partially surrounding the node of the working electrode 451 and a terminal 466 adapted to be electrically coupled to the front-end amplifier 421. Otherwise, the pH sensor 460 is substantially similar to the pH sensor 450 described above as indicated by the reference numerals. The counter electrode 462 is also separated from the working electrode 451 and is also insulated from the wound fluid and the other electrodes by the coating 453 except in the electrical conductive space 454. The counter electrode 462 may be used in connection with the working electrode 451 and the reference electrode 452 for the purpose of error correction of the voltages being measured. For example, the counter electrode 462 may possess the same voltage potential as the potential of the working electrode 451 except with an opposite sign so that any electrochemical process affecting the working electrode 451 will be accompanied by an opposite electrochemical process on the counter electrode 462. Although voltage measurements are still being taken between the working electrode 451 and the reference electrode 452 by the analog front-end device of the pH sensor 460, the counter electrode 462 may be used for such error correction and may also be used for current readings associated with the voltage measurements. Custom printed electrodes assembled in conjunction with a front-end amplifier may be used to partially comprise pH sensors such as the pH sensor 450 and the pH sensor 460 may be available from several companies such as, for example, GSI Technologies, Inc. and Dropsens.

As described above, the sensing portions of the sensors may all be disposed within the therapy cavity 403 and electrically coupled through the circuit board 432 to the front-end amplifier 421 and the communications module 422 mounted on the other side of the circuit board 432 within the component cavity 404. In some embodiments, sensor assembly 425 may comprise a processing element that may include the communications module 422 which may include the microprocessor, and/or the wireless communications chip described above. The processing element may further include the front-end amplifier 421 and any other components that are disposed within the component cavity 404. The processing element may be electrically coupled to the sensing portions of the sensors for receiving property signals from the sensing portions that are indicative of the pressure, humidity, temperature, and the pH of the fluid at the tissue site in order to determine the flow characteristics of the system and the progression of wound healing as described in more detail below.

The systems, apparatuses, and methods described herein may provide other significant advantages. For example, some therapy systems are a closed system wherein the pneumatic pathway is not vented to ambient air, but rather controlled by varying the supply pressure or the pump pressure (PP) to achieve the desired target pressure (TP) in a continuous pressure mode, an intermittent pressure mode, or a variable target pressure mode as described above in more detail with reference to FIGS. 2A and 2B. In some embodiments of the closed system, the wound pressure (WP) being measured in the dressing interface 107 may not drop in response to a decrease in the supply pressure or the pump pressure (PP) as a result of a blockage within the dressing interface 107 or other portions of the pneumatic pathway. In some embodiments of the closed system, the supply pressure or the pump pressure (PP) may not provide airflow to the tissue interface 108 frequently enough that may result in the creation of a significant head pressure or blockages within the dressing interface 107 that also would interfere with sensor measurements being taken by the dressing interface 400 as described above. The head pressure in some embodiments may be defined as a difference in pressure (DP) between a negative pressure set by a user or caregiver for treatment, i.e., the target pressure (TP), and the negative pressure provided by a negative pressure source that is necessary to offset the pressure drop inherent in the fluid conductors, i.e., the supply pressure or the pump pressure (PP), in order to achieve or reach the target pressure (TP). For example, the head pressure that a negative pressure source needs to overcome may be as much as 75 mmHg. Problems may occur in such closed systems when a blockage occurs in the pneumatic pathway of the fluid conductors that causes the negative pressure source to increase to a value above the normal supply pressure or the pump pressure (PP) as a result of the blockage. For example, if the blockage suddenly clears, the instantaneous change in the pressure being supplied may cause harm to the tissue site.

Some therapy systems have attempted to compensate for head pressure by introducing a supply of ambient air flow into the therapeutic environment, e.g., the therapy cavity 403, by providing a vent with a filter on the housing 401 of the dressing interface 400 to provide ambient air flow into the therapeutic environment as a controlled leak. However, in some embodiments, the filter may be blocked when the interface dressing is applied to the tissue site or when asked at least blocked during use. Locating the filter in such a location may also be problematic because it is more likely to be contaminated or compromised by other chemicals and agents associated with treatment utilizing instillation fluids that could adversely affect the performance of the filter and the vent itself.

The embodiments of the therapy systems described herein overcome the problems associated with having a large head pressure in a closed pneumatic environment, and the problems associated with using a vent disposed on or adjacent the dressing interface. More specifically, the embodiments of the therapy systems described above comprise a pressure sensor, such as the pressure sensor 416, disposed within the pneumatic environment, i.e., in situ, that independently measures the wound pressure (WP) within the therapy cavity 403 of the housing 401 as described above rather than doing so remotely. Consequently, the pressure sensor 416 is able to instantaneously identify dangerously high head pressures and/or blockages within the therapy cavity 403 adjacent the manifold 408. Because the auxiliary lumens 435 are not being used for pressure sensing, the auxiliary lumens 435 may be fluidly coupled to a fluid regulator such as, for example, the regulator 118 in FIG. 1, that may remotely vent the therapeutic environment within the therapy cavity 403 to the ambient environment or fluidly couple the therapeutic environment to a source of positive pressure. The regulator 118 may then be used to provide ambient air or positive pressure to the therapeutic environment in a controlled fashion to "purge" the therapeutic environment within both the therapy cavity 403 and the primary lumen 430 to resolve the problems identified above regarding head pressures and blockages, and to facilitate the continuation of temperature, humidity, and pH measurements as described above.

Using a regulator to purge the therapeutic environment is especially important in therapy systems such as those disclosed in FIGS. 1 and 3 that include both negative pressure therapy and instillation therapy for delivering therapeutic liquids to a tissue site. For example, in one embodiment, fluid may be instilled to the tissue site 150 by applying a negative pressure from the negative-pressure source 104 to reduce the pressure at the tissue site 150 to draw the instillation liquid into the dressing 102 as indicated at 302. In another embodiment, liquid may be instilled to the tissue site 150 by applying a positive pressure from the negative-pressure source 104 (not shown) or the instillation pump 116 to force the instillation liquid from the solution source 114 to the tissue interface 108 as indicated at 304. Such embodiments may not be sufficient to remove all the instillation liquids from the therapeutic environment or may not be sufficient to remove the instillation liquids quickly enough from the therapeutic environment to facilitate the continuation of accurate temperature, humidity, and pH measurements. Thus, the regulator 118 may be used to provide ambient air or positive pressure to the therapeutic environment to more completely or quickly purge the therapeutic environment to obtain the desired measurements as described above.

In embodiments of therapy systems that include an air flow regulator comprising a valve such as the solenoid valve described above, the valve provides controlled airflow venting or positive pressure to the therapy cavity 403 as opposed to a constant airflow provided by a closed system or an open system including a filter in response to the wound pressure (WP) being sensed by the pressure sensor 416. The controller 110 may be programmed to periodically open the solenoid valve as described above allowing ambient air to flow into the therapy cavity 403, or applying a positive pressure into the therapy cavity 403, at a predetermined flow rate and/or for a predetermined duration of time to purge the pneumatic system including the therapy cavity 403 and the primary lumen 430 of bodily liquids and exudates so that the humidity sensor 418 and the pH sensor 420 provide more accurate readings and in a timely fashion. This feature allows the controller to activate the solenoid valve in a predetermined fashion to purge blockages and excess liquids that may develop in the fluid pathways or the therapy cavity 403 during operation. In some embodiments, the controller may be programmed to open the solenoid valve for a fixed period of time at predetermined intervals such as, for example, for five seconds every four minutes to mitigate the formation of any blockages.

In some other embodiments, the controller may be programmed to open the solenoid valve in response to a stimulus within the pneumatic system rather than, or additionally, being programmed to function on a predetermined therapy schedule. For example, if the pressure sensor is not detecting pressure decay in the canister, this may be indicative of a column of fluid forming in the fluid pathway or the presence of a blockage in the fluid pathway. Likewise, the controller may be programmed to recognize that an expected drop in canister pressure as a result of the valve opening may be an indication that the fluid pathway is open. The controller may be programmed to conduct such tests automatically and routinely during therapy so that the patient or caregiver can be forewarned of an impending blockage. The controller may also be programmed to detect a relation between the extent of the deviation in canister pressure resulting from the opening of the valve and the volume of fluid with in the fluid pathway. For example, if the pressure change within the canister is significant when measured, this could be an indication that there is a significant volume of fluid within the fluid pathway. However, if the pressure change within the canister is not significant, this could be an indication that the plenum volume was larger.

The systems, apparatuses, and methods described herein may provide other significant advantages over dressing interfaces currently available. For example, a patient may require two dressing interfaces for two tissue sites, but wish to use only a single therapy device to provide negative pressure to and collect fluids from the multiple dressing interfaces to minimize the cost of therapy. In some therapy systems currently available, the two dressing interfaces would be fluidly coupled to the single therapy device by a Y-connector. The problem with this arrangement is that the Y-connector embodiment would not permit the pressure sensor in the therapy device to measure the wound pressure in both dressing interfaces independently from one another. A significant advantage of using a dressing interface including in situ sensors, e.g., the dressing interface 400 including the sensor assembly 425 and the pressure sensor 416, is that multiple dressings may be fluidly coupled to the therapy unit of a therapy system and independently provide pressure data to the therapy unit regarding the associated dressing interface. Each dressing interface 400 including in situ sensors that is fluidly coupled to the therapy unit for providing negative pressure to the tissue interface 108 and collecting fluids from the tissue interface 108 has the additional advantage of being able to collect and monitor other information at the tissue site including, for example, humidity data, temperature data, and the pH data being provided by the sensor assembly 425 in addition to the pressure data and other data that might be available from other sensors in the sensor assembly 425.

Another advantage of using the dressing interface 400 that includes a pressure sensor in situ such as, for example, the pressure sensor 416, is that the pressure sensor 416 can more accurately monitor the wound pressure (WP) at the tissue site and identify blockages and fluid leaks that may occur within the therapeutic space or other distribution components of the system as described in more detail above. Another advantage of using the dressing interface 400 that includes a pressure sensor in situ is that one of the auxiliary lumens 435 are freed up to vent or actively purge the sensing portions of the sensors within the therapeutic cavity 403 so that meaningful data regarding the sensing properties can be obtained on a timely basis for providing the therapy and detecting the flow characteristics of the system and the status of wound healing. Yet another advantage of using a dressing interface including in situ sensors, e.g., the dressing interface 400, is that the sensor assembly 425 provides additional data including pressure, temperature, humidity, and pH of the fluids being drawn from the tissue site that facilitates improved control algorithms for detecting flow characteristics within the system and profiling the status of wound healing. Such improvements further assist the caregiver with additional information provided by the therapy unit of the therapy system to optimize the wound therapy being provided and the overall healing progression of the tissue site when combined with appropriate control logic.

As indicated above, the processing element of the sensor assembly 425 may receive property signals indicative of the pressure, the humidity, the temperature, and the pH within the therapy cavity 403 that may be transmitted to the controller 110 of the system for applying therapy to the tissue site and detecting the flow characteristics of the system and the status of wound healing at the tissue site. In some embodiments, the flow characteristics may include the detection of blockages, fluidly leaks, air leaks, and desiccation conditions associated with the dressing interface and the system. The property signals associated with the fluids at a specific time may be processed and logged by the controller 110 and assessed with previous property signal measurements. The controller 110 may also be programmed with a negative pressure control algorithm that assesses the logged property signals to assess the status of wound healing and with that assessment adjust the pump pressure (PP) and/or the pump duty cycle (PD) if necessary to maintain the wound pressure (WP) proximate the desired target pressure (TP).

Figure 10:
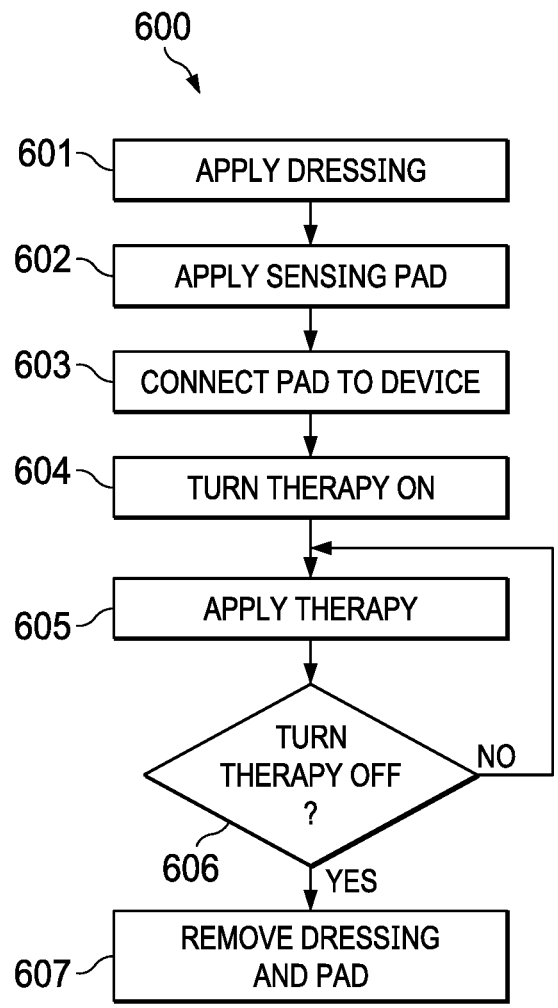
FIG. 10 is a flow chart illustrating a method for treating a tissue site utilizing the dressing interface of FIG. 4 for applying negative-pressure therapy and sensing properties of wound exudates extracted from the tissue site.

Referring to FIG. 10, a flowchart is shown that illustrates a method for treating a tissue site in some embodiments of therapy systems including, for example, the therapy system 100. More specifically, such method may utilize a dressing interface or sensing pad such as, for example, the dressing interface 400 of FIG. 4, for applying negative-pressure therapy and sensing properties of wound exudates extracted from a tissue site as shown at 600. A tissue interface such as the tissue interface 108 may be placed within, over, on, or otherwise proximate a tissue site at 601. A cover such as the cover 106 may be placed over the tissue interface 108 and sealed to an attachment surface near the tissue site 150. For example, the cover 106 may be sealed to undamaged epidermis peripheral to a tissue site. Thus, the dressing 102 provides a sealed therapeutic environment proximate to a tissue site, substantially isolated from the external environment, while the negative-pressure source 104 reduces the pressure within the sealed therapeutic environment. In some embodiments, the method may further comprise applying the sensing pad or dressing interface to the tissue interface at 602. More specifically, applying the sensing pad may include positioning the housing on the dressing interface so that the aperture of the housing is in fluid communication with the tissue interface. The dressing interface may comprise a wall disposed within the housing to form a therapy cavity within the housing and a component cavity fluidly sealed from the therapy cavity, wherein the therapy cavity opens to the aperture as described above. Such dressing interface may further comprise a negative-pressure port fluidly coupled to the therapy cavity and adapted to be fluidly coupled to a negative-pressure source as described above. The dressing interface may further comprise a processing element disposed in the component cavity or outside the therapy cavity, similar to the processing element described above.

Referring to 603, the method may further comprise connecting the sensing pad to a wound therapy device such as, for example, the therapy system 100. Connecting the sensing pad may include coupling the therapy cavity of the sensing pad to a negative-pressure source and to a vent as described above, and electrically coupling the processing element to a controller of the therapy system such as, for example, the controller 110. The sensing pad or the dressing interface may further comprise a pH sensor, a temperature sensor, a humidity sensor, and a pressure sensor, each having a sensing portion disposed within the therapy cavity and each electrically coupled to the processing element through the wall as described above. Referring to 604, the method may further comprise turning on the therapy system and applying a desired therapy that may include negative pressure therapy, instillation therapy, or other therapy for treating the tissue site as indicated at 605. In some embodiments, for example, the method may comprise applying negative-pressure therapy to the therapy cavity of the dressing interface to draw fluids from the tissue interface into the therapy cavity and exiting out of the reduced-pressure port. The method may further comprise sensing the pH, temperature, humidity, and pressure properties of the fluids flowing through therapy cavity utilizing the sensing portion of the sensors which may provide property signals indicative of such properties to the processing element. Applying negative-pressure therapy may further comprise providing the property signals from the processing element to the controller of the therapy system for processing the property signals and treating the tissue site in response to the property data being collected and processed by the therapy system. Referring to decision block 606, the method may further comprise turning off the therapy treatment when receiving a signal from a caregiver, a patient, or from a control algorithm stored on the controller of the therapy system itself. If the therapy system is turned off (YES), the method may further comprise removing the dressing interface, the cover, and the sensing pad after the therapy system is turned off as indicated at 607. If no such signal is received, the method loops back to 605 to continue applying the negative-pressure therapy to the dressing interface and the tissue site, which may include commands provided by the control algorithm to further control the negative pressure therapy being provided by increasing the pump pressure (PP) or the pump duty cycle (PD) for example.

Figure 11:
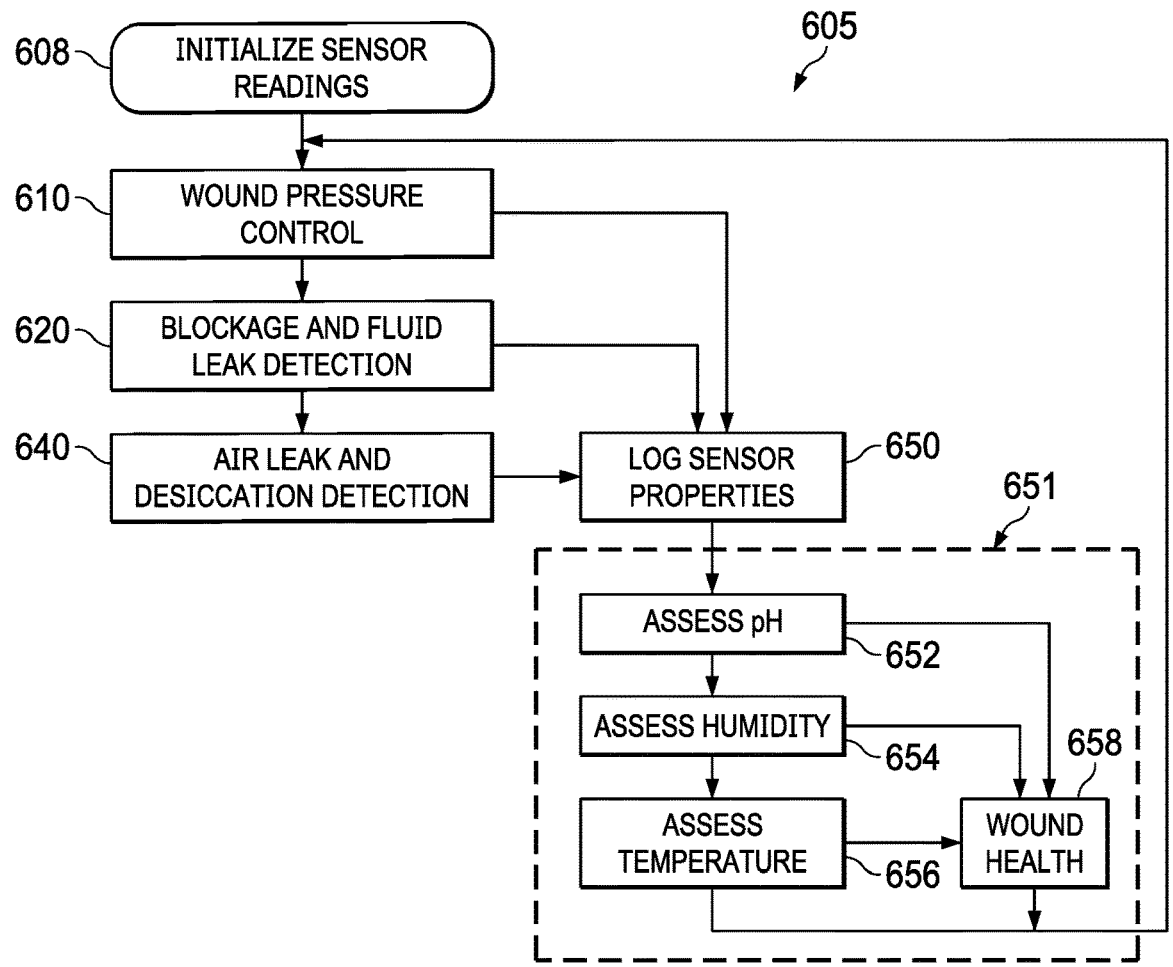
FIG. 11 is a schematic block diagram illustrating a negative pressure control algorithm utilized within the tissue treatment method of FIG. 10 including the detection of dressing flow characteristics within the system and the assessment of sensor properties.
Figure 13A:
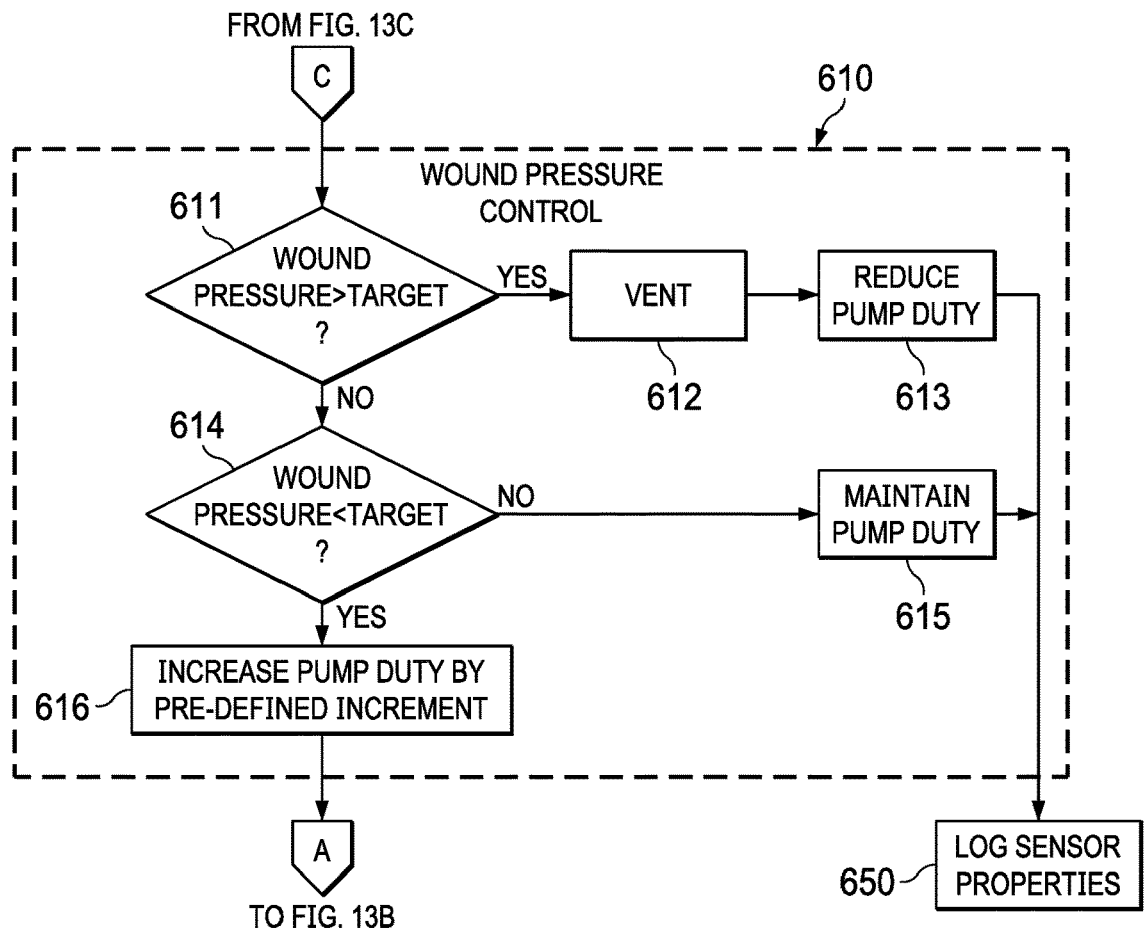
FIG. 13A is a flow chart illustrating a wound pressure control method configured to operate in the negative pressure control algorithm of FIG. 11.
Figure 13C:
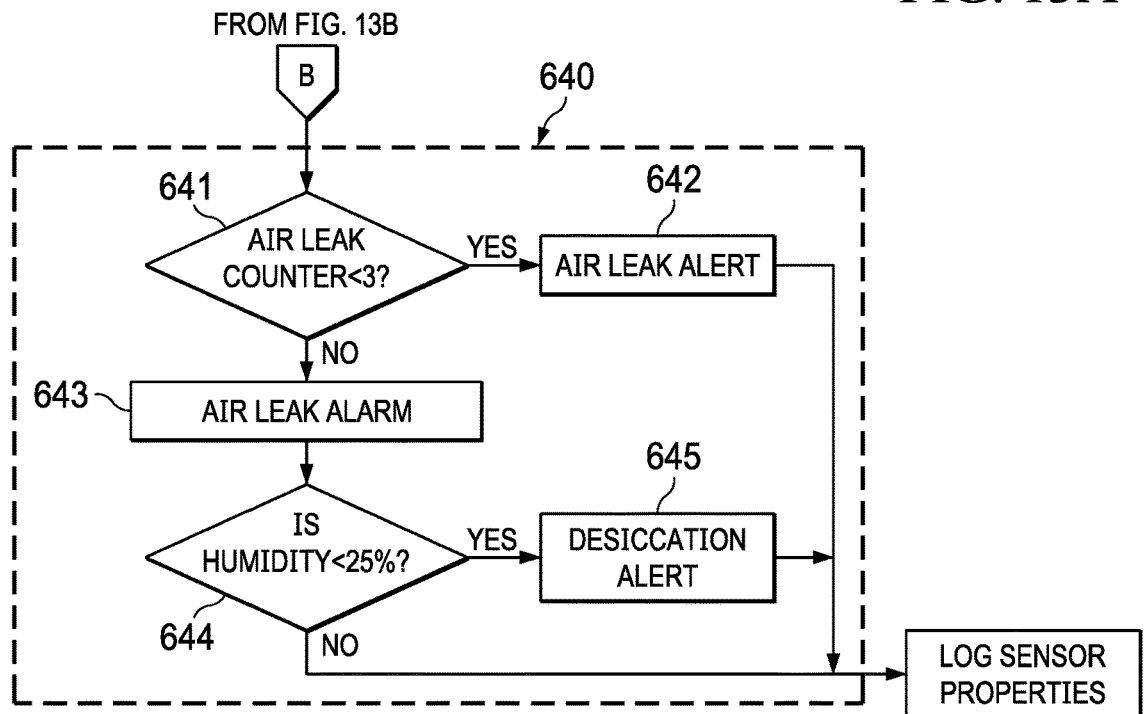
FIG. 13C is a flow chart illustrating a method for detecting air leaks and desiccation as two of the dressing flow characteristics of FIG. 11, and for logging and assessing the sensing properties.
Figure 13B:
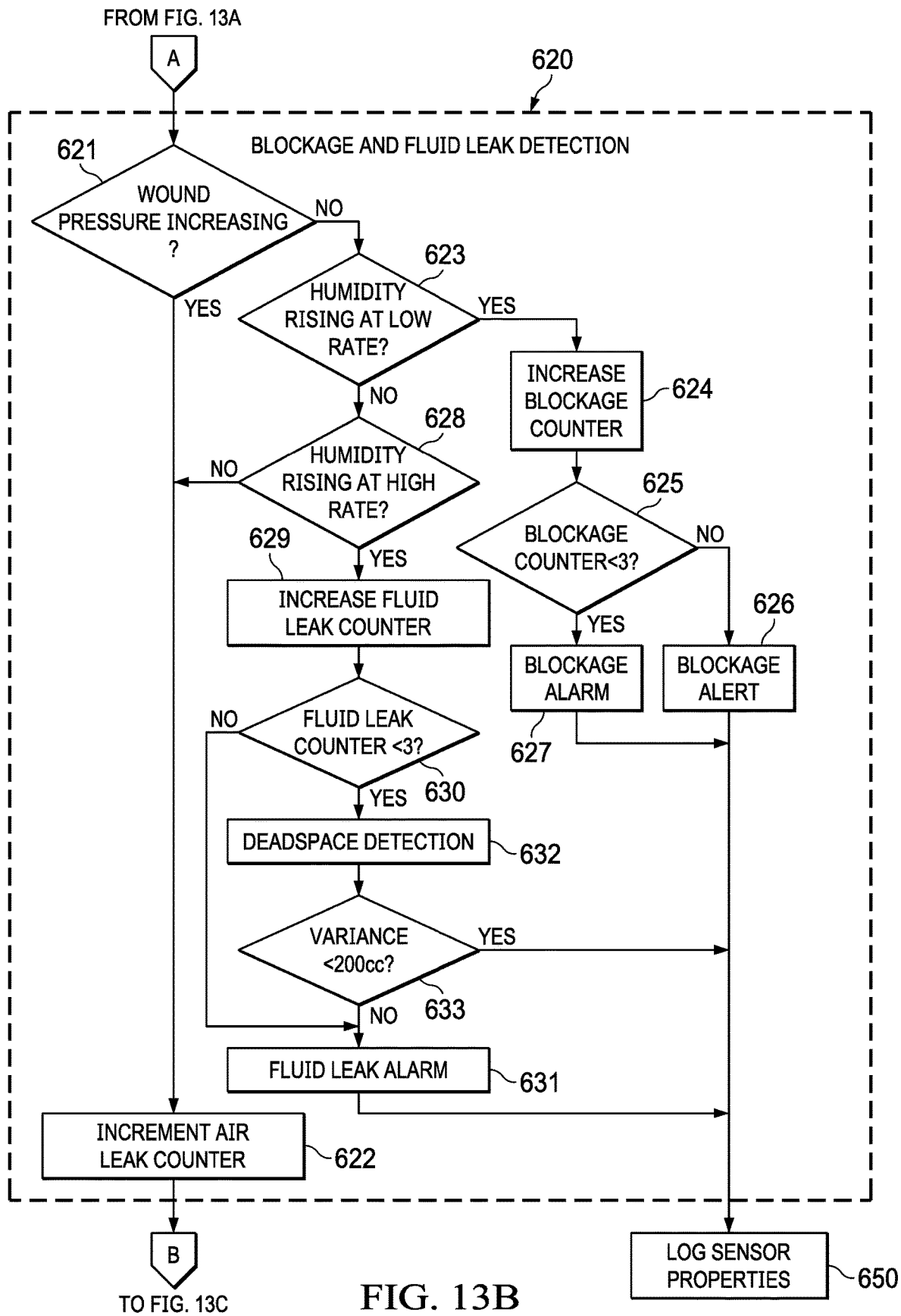
FIG. 13B is a flow chart illustrating a method for detecting blockages and fluid leaks as two of the dressing flow characteristics of FIG. 11.

FIG. 11 is a schematic block diagram illustrating an embodiment of a control algorithm that may comprise a negative pressure control algorithm that may be utilized when applying the negative-pressure therapy within the tissue treatment method 600, hereinafter referred to as the negative pressure control algorithm 605. The negative pressure control algorithm 605 may include the detection of dressing flow characteristics within the system and an assessment of sensor properties based on the property data stored on the controller of the therapy system. FIGS. 13A-13C show flow charts illustrating various methods of some embodiments that may be configured to operate within the negative pressure control algorithm 605 of FIG. 11. The negative pressure therapy algorithm 605 may commence by initializing the sensor readings at 608 by setting initial values of the property signals provided by the sensors to the processing element of the dressing interface and ultimately to the controller of the therapy system as indicated for processing and assessment.

The negative pressure control algorithm 605 may include a wound pressure control 610 as shown in FIG. 11 that compares wound pressure (WP) to the target pressure (TP), and then provides commands to increase or decrease the pump duty cycle (PD) accordingly and/or log the sensor properties at 650. Referring more specifically to FIG. 13A, if the wound pressure (WP) is greater than the target pressure (TP) at 611 (YES), the wound pressure control 610 may generate a command to vent the therapy cavity at 612 as described above and a command to reduce the pump duty cycle (PD) at 613. After the pump duty cycle (PD) is reduced, the property signals may then be logged in the controller of the therapy system as indicated at 650 for further processing by a set of assessment algorithms as indicated at 651. If the wound pressure (WP) is not greater than the target pressure (TP) at 611 (NO), the wound pressure (WP) is again compared to the target pressure (TP) at 614. If the wound pressure (WP) is not less than the target pressure (TP), i.e., greater than or equal to the target pressure (TP), the wound pressure control 610 may generate a command to maintain or reduce the pump duty cycle (PD) at 615 and the property signals may then be logged in the controller of the therapy system as indicated at 650 for further processing by the assessment algorithms 651. However, if the wound pressure (WP) is less than or equal to the target pressure (TP), the wound pressure control 610 may generate a command to increase the pump duty cycle (PD) at 616. When the pump duty cycle (PD) is increased, the negative pressure control algorithm 605 in some embodiments may proceed to dressing-alert algorithms including, for example, a blockage detection algorithm and fluid leak detection algorithm shown generally at 620 in FIG. 11 (shown more specifically in FIG. 13B), and an air leak detection algorithm and desiccation detection algorithm shown generally at 640 in FIG. 11 (shown more specifically in FIG. 13C).

Figure 12:
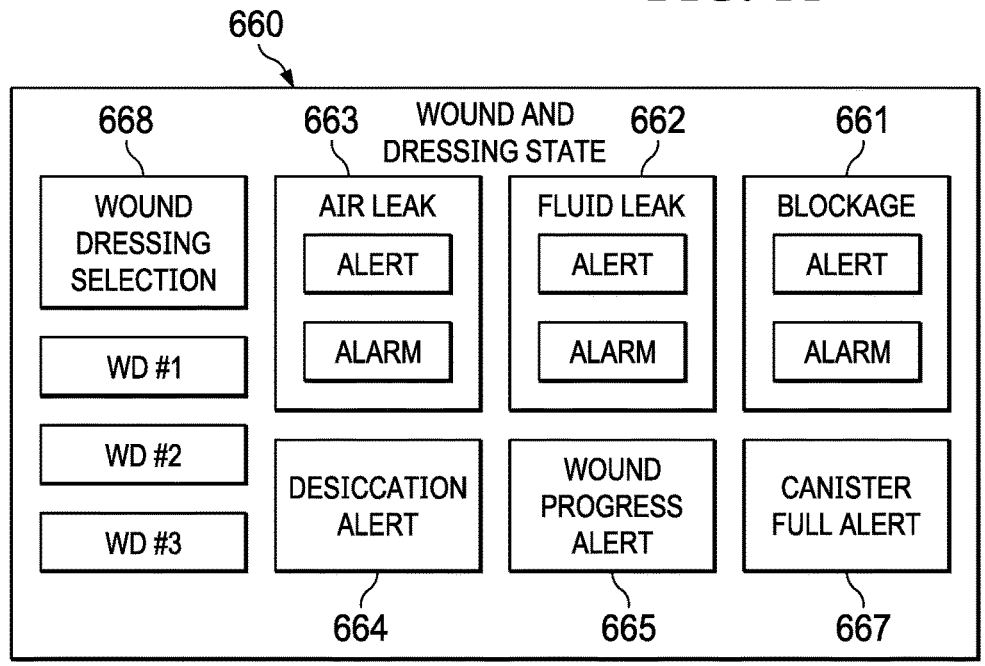
FIG. 12 is a block diagram of a user interface illustrating alerts and alarms associated with the dressing flow characteristics of FIG. 11.

In some embodiments of a therapy system such as, for example, therapy system 100, the therapy system may comprise a user interface coupled to the controller 110. Referring more specifically to FIG. 12, a block diagram of one example embodiment of a user interface, user interface 660, that may comprise a variety of alerts and alarms associated with the dressing flow characteristics of FIG. 11. These alerts and/or alarms associated with the dressing flow characteristics may comprise, for example, alerts and/or alarms for a blockage condition 661, a fluid leak condition 662, an air leak condition 663, or a desiccation condition 664. The negative pressure control algorithm may be programmed to generate an alarm based on the occurrence of a predetermined number of alerts such as, for example, generating alarm after the occurrence of three alerts. The user interface 660 may also provide alerts and/or alarms that may be associated with wound progress 665 and/or canister-full detection 667 based on the fluid properties being provided by the sensing pad or the dressing interface 400, for example. All of the fluid properties and associated alerts and/or alarms identified above may be selectively provided for each wound dressing (WD #1, WD #2 or WD #3) such as, for example, wound dressings substantially similar to the dressing 102, that may be fluidly and electrically coupled to the therapy system 100. For example, a patient or caregiver may select a desired wound dressing by setting a wound dressing selection switch 668. Alternatively, the controller of the therapy system may be programmed to selectively collect the fluid properties and provide alerts and/or alarms based on a predetermined order with times designated for each wound dressing.

After the negative pressure control algorithm 605 proceeds to the dressing-alert algorithms including, for example, the blockage detection algorithm and fluid leak detection algorithm, or a blockage/leak detection algorithm, shown generally at 620 in FIG. 13B, the algorithm may commence with determining whether the wound pressure (WP) is increasing at 621 after increasing the pump duty cycle (PD) at 616 by a predetermined increment as an output of the wound pressure control 610. If the wound pressure (WP) responds and is increasing, the algorithm may increment an air leak counter at 622 and proceed to the air leak detection algorithm and desiccation detection algorithm at 640. However, if the wound pressure (WP) does not increase, the blockage/leak detection algorithm 620 determines whether the property signals associated with the humidity, i.e., the humidity data, is rising at a relatively low rate within the therapy cavity at 623. If the humidity data is rising at a relatively low rate, the blockage/leak detection algorithm 620 increments a blockage counter 624 and inquires whether the blockage counter is less than a predetermined blockage count threshold at 625 such as, for example, less than three, to determine whether a blockage alert or alarm should be generated. If the blockage counter number is less than the blockage count threshold, the blockage/leak detection algorithm 620 generates a blockage alert at 626 and progresses to log a new set of sensor properties at 650. If the blockage counter number is greater than or equal to the blockage count threshold, the negative pressure control algorithm generates a blockage alarm at 627 and progresses to log a new set of sensor properties at 650.

If the humidity data is not rising at a relatively low rate at 623, the negative pressure control algorithm inquires whether the humidity data is increasing at a high rate at 628. If the humidity data is not increasing at such a high rate, the blockage/leak detection algorithm 620 increments the air leak counter 622 and proceeds to the air leak detection algorithm and desiccation detection algorithm at 640. However, if the humidity data is increasing above the high rate, the blockage/leak detection algorithm 620 increments or increases a fluid leak counter at 629 and inquires whether the fluid leak counter is less than a predetermined fluid count threshold at 630 such as, for example, less than three. If the fluid leak counter number is not less than the fluid count threshold, alternatively greater than or equal to the fluid count threshold, the blockage/leak detection algorithm 620 generates a fluid leak alarm at 631 and progresses to log a new set of sensor properties at 650. If the fluid leak counter number is less than the blockage count threshold, the blockage/leak detection algorithm 620 checks the dead space detection at 632 that may be associated with the amount of gas or space that may be present in the container of the therapy system such as, for example, the container 112, after collecting liquids in the container. The blockage/leak detection algorithm 620 determines whether there is a dead space detection variance of less than a predetermined value, e.g., 200 cc, at 633. If the variance is not less than the predetermined value, i.e., if the variance is greater than the predetermined value, the blockage/leak detection algorithm 620 generates a fluid leak alarm at 631. If the blockage/leak detection algorithm 620 determines that the variance is less than the predetermined value at 633, the blockage/leak detection algorithm 620 generates and canister full alert 667 (not shown in FIG. 13A) and then progresses to log a new set of sensor properties at 650.

After the negative pressure control algorithm 605 proceeds to the dressing-alert algorithms including, for example, the air leak detection algorithm and desiccation detection algorithm at 640, or a desiccation/leak detection algorithm, shown generally at 640 in FIG. 13C, the algorithm may commence by determining at 641 whether the air leak counter at 622 is less than a predetermined air count threshold at 641 such as, for example, less than three, after incrementing the air leak counter as described above. If the air leak counter 641 is less than the air count threshold, the negative pressure control algorithm may generate an air leak alert at 642 and progress to log a new set of sensor properties at 650. If the air leak counter 641 is not less than the air count threshold, alternatively if the air leak counter is greater than or equal to the air count threshold, the desiccation/leak detection algorithm 640 may generate an air leak alarm at 643 and proceed to inquire whether the humidity is less than about a predetermined internal humidity value at 644. More specifically, if the humidity within the therapy cavity of the sensing pad measured by the humidity sensor 418 is less than a percentage value of the ambient humidity (ambient humidity sensor not shown) such as, for example, a percentage value of 25%, the desiccation/leak detection algorithm 640 may generate a desiccation alert at 645 and proceed to log new set of sensor properties at 650. Alternatively, if the humidity within the therapy cavity of the sensing pad is greater than a humidity percentage of 25%, for example, the desiccation/leak detection algorithm 640 would not generate a desiccation alert, but rather would proceed to log new set of sensor properties at 650.

Referring back to FIG. 11, a new set of property signals indicative of the sensor properties may be logged at 650 into the controller of the therapy system as a result of the alerts, alarms, and other events described above with respect to the negative pressure control algorithm 605 including the wound pressure control 610, the blockage detection and fluid leak detection algorithms 620, and the air leak detection algorithm and desiccation detection algorithm at 640. Logging these property signals along with contemporaneous readings of the wound pressure (WP), the pump pressure (PP), and the pump duty cycle (PD) generates sets of property data that may include humidity data, temperature data, and pH data being provided by the processing element such as, for example, the sensor assembly 425, in addition to the pressure data, duty cycle data, and other data that might be available from other sensors in the therapy system 100 that may be coupled to the controller or other distribution components in the therapy system. In some embodiments, the negative pressure control algorithm 605 may be configured to assess the pH data at 652, the humidity data at 654, and the temperature data at 656, and use such data to assess the status of wound health of the tissue site at 658, and further configured to return to the wound pressure control 610 after the assessments have been completed. In some embodiments, the assessments may include an analysis of whether the data is increasing or decreasing and how rapidly the data may be increasing or decreasing. In some embodiments, the assessments may further include an analysis of whether the data may increase or decrease and how rapidly that data may fluctuate in each direction. In some embodiments, the assessment may further include a determination that the relevant data is simply not affected.

The assessments of the pH data, the humidity data, and the temperature data along with contemporaneous wound pressure (WP) data, pump pressure (PP) data, and the pump duty cycle (PD) data may be utilized to determine how the flow characteristics of the therapy system 100 may be affected a blockage, a fluid leak, an air leak, or desiccation within the system including the sensor pad or dressing interface 400. Referring more specifically to Table 1, the flow characteristics may include a blockage state condition within the therapy system that may be identified by the assessment of the pH data, the humidity data, and the temperature data along with contemporaneous wound pressure (WP) data, pump pressure (PP) data, and the pump duty cycle (PD) data.

TABLE 1

| Inputs | Dressing State: Flow Characteristics | | |
| --- | --- | --- | --- |
| | Blockage | Fluid Leak (Bolus) | Air Leak |
| Wound Pressure (WP) Sensor Assembly | WP may slowly decrease ↓ | WP will decrease ↓ | WP may decrease ↓ |
| Wound Humidity (Hum) Sensor Assembly | Humidity may increase slowly ↑ | Humidity will increase ↑ | Humidity may change rapidly ↑ |
| Wound Temperature (Temp) Sensor Assembly | Temperature may increase slowly ↑ | Temperature may increase ↑ | Temperature may change ↓ |
| Pump Duty (PD) System | PD will increase ↑ | PD may increase ↑ | PD will increase ↑ |
| Pump Pressure (PP) System | PP will increase ↑ | PP may increase for a short time ↓ | PP may increase ↑ |

Figure 14:
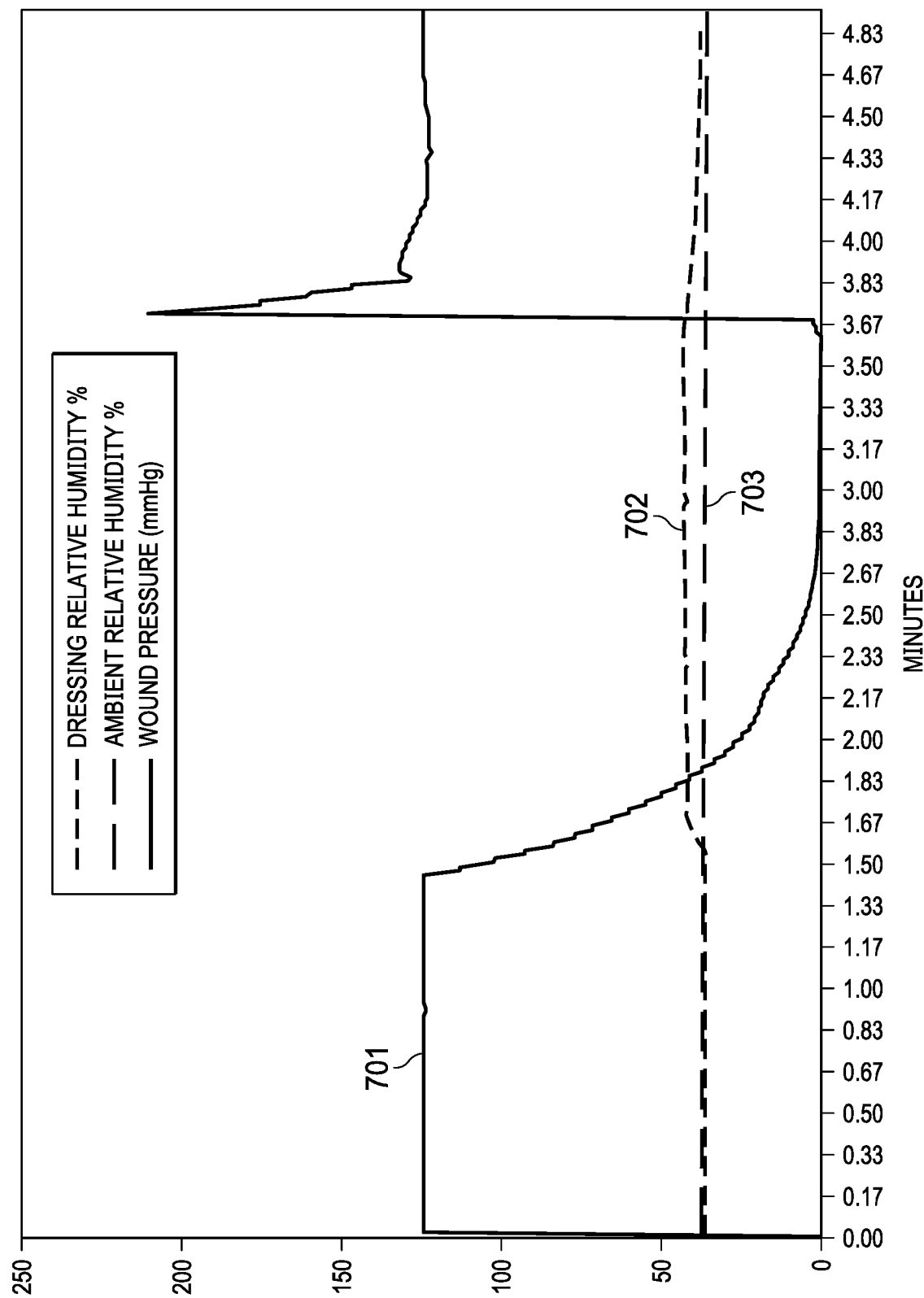
FIG. 14 is a graph illustrating data associated with the detection of blockages based on the assessment of humidity data and wound pressure over time generated by the negative pressure control algorithm of FIG. 11.

For example, a blockage state condition may be identified in the system (e.g., a substance blocking a tube or a kink in the tube) when the pump pressure (PP) data increases and the pump duty cycle (PD) data increases. In some embodiments, the blockage state condition may be identified further if the wound pressure (WP) data slowly decreases. In yet other embodiments, the blockage state condition may be identified further if the humidity data slowly increases, especially if the wound dressing is saturated with fluids. In yet other embodiments, the blockage state condition may be identified further if the temperature data slowly increases. In still other embodiments, the blockage state condition may be identified further when the pH data is not affected. Referring to FIG. 14 as an example, a graph is shown illustrating test results using the dressing interface 400 for the detection of blockages based on the assessment of humidity data and wound pressure over time generated by the negative pressure control algorithm 605 of FIG. 11. The wound pressure (WP) being applied at the tissue site is set as a target pressure (TP) of 125 mmHg. As can be seen, a blockage state condition is identified at approximately 1.50 minutes when the wound pressure (WP) 701 begins to decrease and the dressing humidity 702 slowly increases over the ambient humidity 703 as described above. In some embodiments, the negative pressure control algorithm 605 may generate a command to provide an alarm 661 and shut down the pump 104, for example, until the blockage can be removed. When the blockage is removed at 3.67 minutes, the wound pressure (WP) returns to the target pressure (TP) and the dressing humidity converges back to the ambient humidity.

Figure 15:
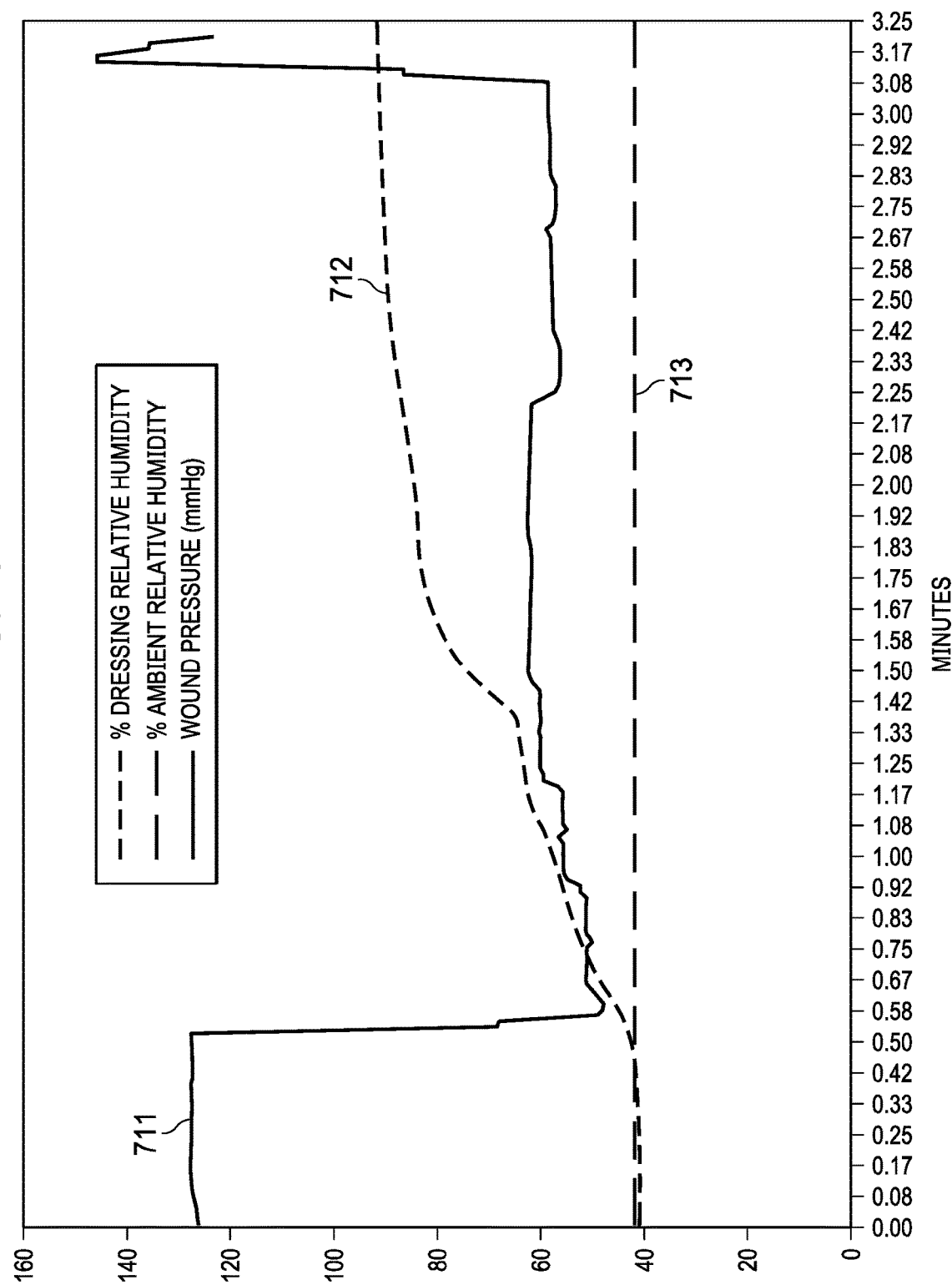
FIG. 15 is a graph illustrating data associated with the detection of fluid leaks based on the assessment of humidity data and wound pressure data over time generated by the negative pressure control algorithm of FIG. 11.

Still referring more specifically to Table 1, the flow characteristics may include a fluid leak state within the therapy system that also may be identified by the assessment of the pH data, the humidity data, and the temperature data along with contemporaneous wound pressure (WP) data, pump pressure (PP) data, and the pump duty cycle (PD) data. For example, a fluid leak state may be identified in the wound dressing if the pump duty cycle (PD) data and the pump pressure (PP) data increase depending on the severity of a fluid bolus trapped in the wound dressing. The pump pressure (PP) data may increase for only a short period of time. In some embodiments, the fluid leak state may be identified further if the wound pressure (WP) data decreases but will typically track with the pump pressure (PP) data. In yet other embodiments, the fluid leak state may be identified further if the humidity data increases as a result of higher exudates or blood volumes collecting at the tissue site. The temperature data may also increase in a corresponding fashion. In still other embodiments, the fluid leak state may be identified further when the pH data is not affected. Referring to FIG. 15 as an example, a graph is shown illustrating test results using the dressing interface 400 for the detection of fluid leaks based on the assessment of humidity data and wound pressure data over time generated by the negative pressure control algorithm of FIG. 11. The wound pressure (WP) being applied at the tissue site is set as a target pressure (TP) of 125 mmHg. A bolus of 60 cc of simulated wound fluid with a viscosity of about 16 cP was rapidly introduced into the wound dressing. As can be seen, a fluid leak state is identified at approximately 0.50 minutes when the wound pressure (WP) 711 begins to decrease and the dressing humidity 712 slowly increases over the ambient humidity 713 as described above. In some embodiments, the negative pressure control algorithm 605 may generate a command to provide an alarm 662 and shut down the pump 104, for example, until the fluid leak can be corrected. Clearly, such assessment facilitates the detection of liquid boluses or potentially adverse events such as a blood vessel that bursts, so that a caregiver may be alerted to a potentially dangerous situation so that a timely intervention is possible.

Referring more specifically to Table 2, the flow characteristics may include an air leak state within the therapy system that may be identified by the assessment of the pH data, the humidity data, and the temperature data along with contemporaneous wound pressure (WP) data, pump pressure (PP) data, and the pump duty cycle (PD) data.

TABLE 2

| Inputs | Dressing State: Flow Characteristics | |
|---|---|---|
| | Air Leak | Desiccation |
| Wound Pressure (WP) Sensor Assembly | WP may decrease ↓ | WP likel unaffected ↓ |
| Wound Humidity (Hum) Sensor Assembly | Humidity may change rapidly ↑ | Humidity will decrease ↓ |
| Wound Temperature (Temp) Sensor Assembly | Temperature may change ↑ | Temperature may change ↑ |
| Pump Duty (PD) System | PD will increase ↑ | PD likely unaffected ↑ |
| Pump Pressure (PP) System | PP may increase ↑ | PP likely unaffected ↑ |

Figure 16:
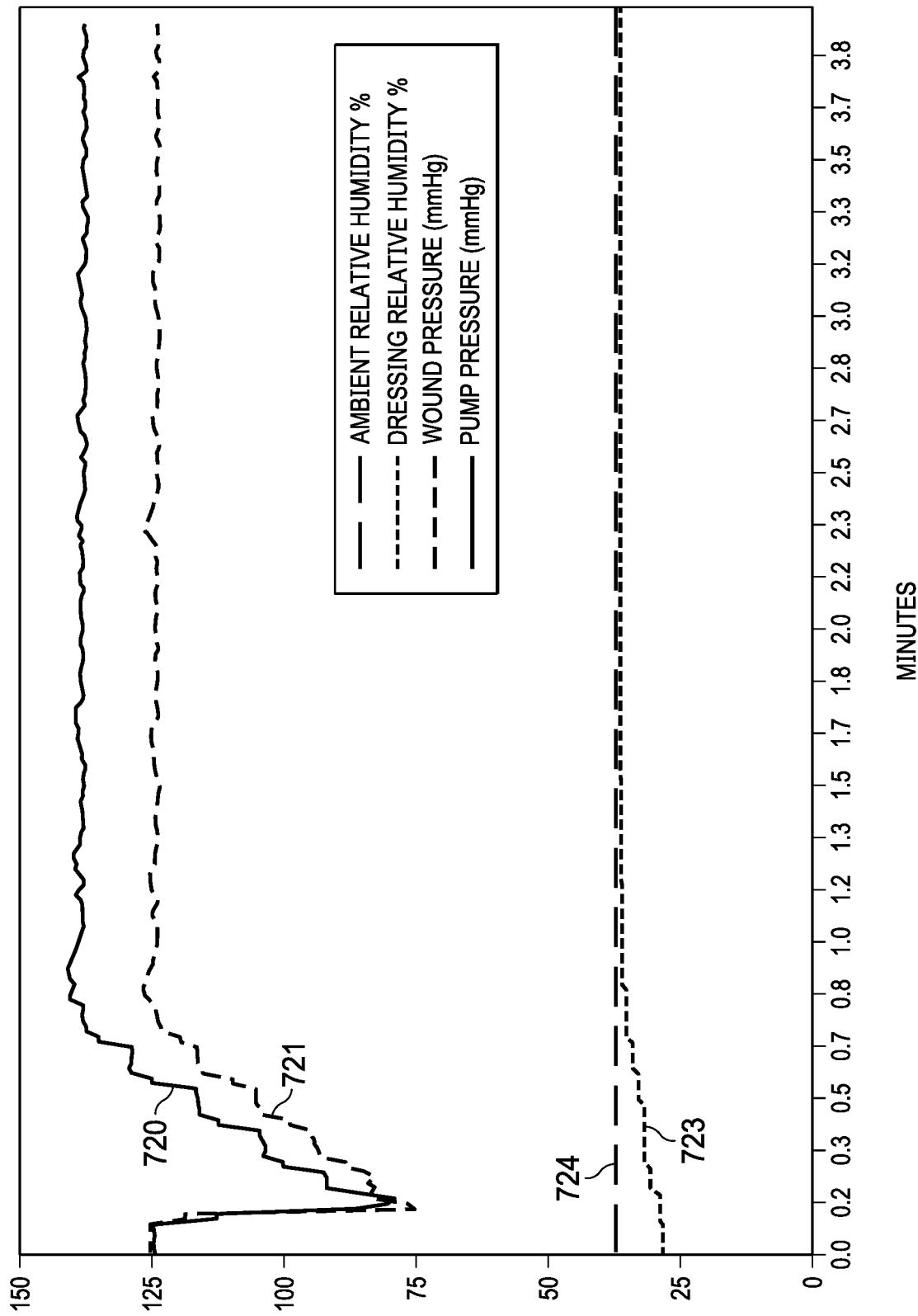
FIG. 16 is a graph illustrating data associated with the detection of air leaks based on the assessment of humidity data, wound pressure data, and pump pressure data over time generated by the negative pressure control algorithm of FIG. 11.

For example, an air leak state within the therapy system that may be identified when the pump duty cycle (PD) data increases proportionally with the severity of the leak, and wherein the pump pressure (PP) data may increase or nonresponsive to an increase in the pump duty cycle (PD) data again depending on the severity of the leak. The air leak may be sufficiently severe to require an increase in both the pump duty cycle (PD) and the pump pressure (PP). In some embodiments, the air leak state may be identified further if the wound pressure (WP) begins to decrease proportionally with the severity of the leak but will track with the pump pressure (PP). In yet other embodiments, the air leak state may be identified further if the humidity data changes rapidly depending upon the environmental humidity measured by the system and the saturation level of the wound dressing. For example, if the air is drier than the saturation level of the wound dressing, then the humidity of the dressing may decrease. The air leak state may also be identified further if the temperature data changes depending on the environmental temperature and the saturation level of the wound dressing. For example, the temperature data will decrease if the environmental temperature is cooler than the temperature at the tissue site. In still other embodiments, the air leak state may be identified further when the pH data is not affected. Referring to FIG. 16 as an example, a graph is shown illustrating test results using the dressing interface 400 for the detection of air leaks based on the assessment of humidity data, wound pressure data, and pump pressure data over time generated by the negative pressure control algorithm of FIG. 11. The wound pressure (WP) being applied at the tissue site is set as a target pressure (TP) of 125 mmHg. A small leak was introduced into the wound dressing such that the pump pressure (PP) had to be elevated to approximately 140 mmHg in order to maintain a wound pressure (WP) at the target pressure (TP). As can be seen, an air leak state is identified at approximately 0.2 minutes when the wound pressure (WP) 721 decreases and the pump pressure (PP) 722 increases to compensate for the decreasing wound pressure (WP). In some embodiments, the air leak state also may be identified by the dressing humidity 723 which slowly increases to converge with the ambient humidity 724. In this example, the tissue interface was dry, so that the humidity increased with the introduction of the leak (ambient humidity). In other embodiments, the air leak state also may be identified by the dressing humidity 723 which slowly decreases to converge with the ambient humidity 724.

In some embodiments where the humidity data decreases indicating that the wound is drying out, the negative pressure control algorithm 605 may generate a command to provide an alarm 663 and shut down the pump 104 until the air leak can be corrected. In other embodiments where the humidity does not decrease or is at an acceptable level, the negative pressure control algorithm 605 may generate a command to provide an alarm or an alert 663, but continue providing therapy by increasing the pump duty cycle (PD) to compensate for the air leak. Referring back to Table 1, an air leak state may be distinguished from a fluid leak state because the humidity data will increase in the presence of a fluid leak, but will not increase in the presence of an air leak (although it may fluctuate rapidly). Clearly, such assessment facilitates the detection of air leaks by differentiating them from fluid leaks, so that the therapy system may continue providing negative pressure therapy by increasing the pump duty cycle (PD) to compensate for the air leak rather than discontinuing the therapy being provided.

Figure 17:
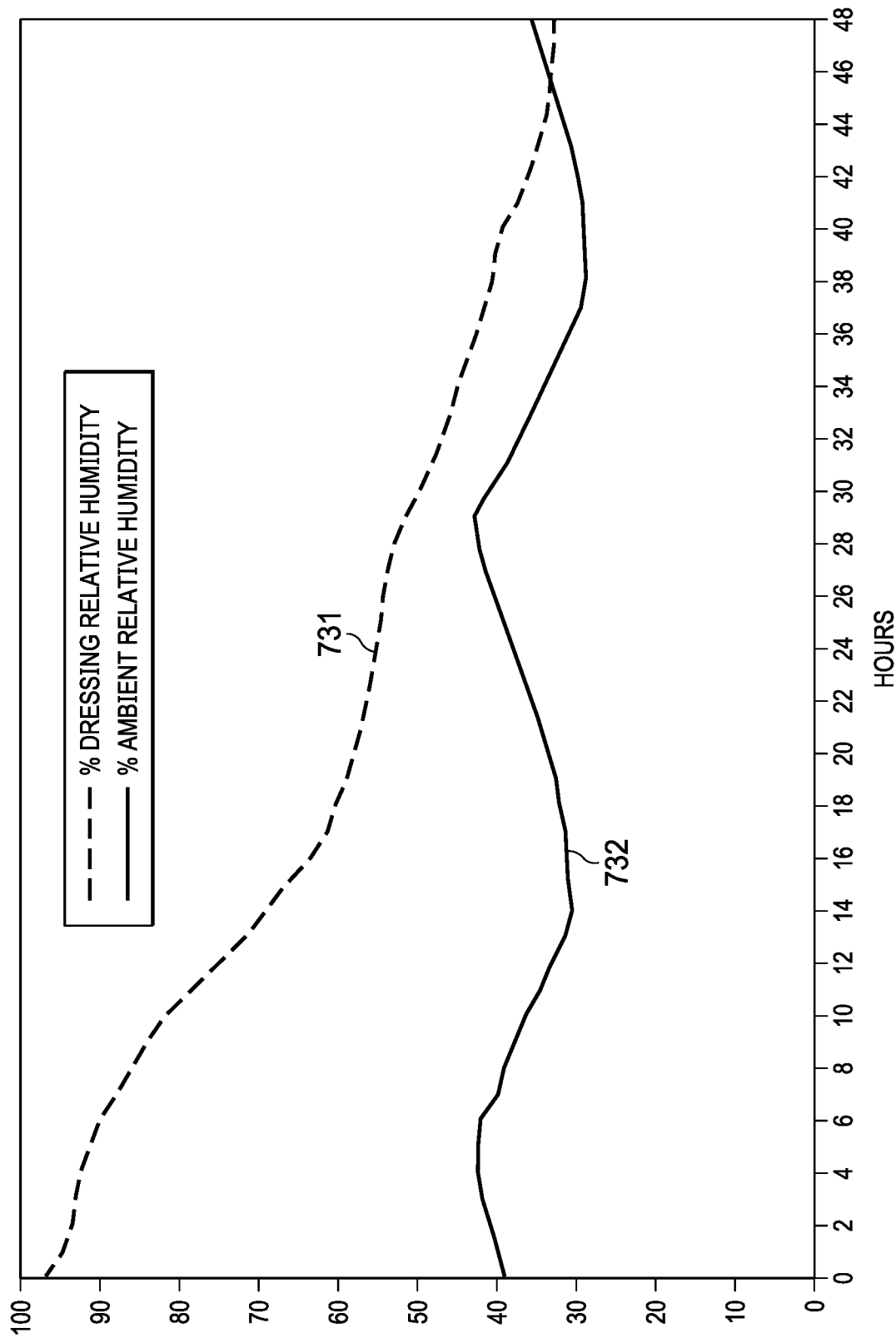
FIG. 17 is a graph illustrating data associated with the detection of desiccation conditions based on the assessment of humidity data over time generated by the negative pressure control algorithm of FIG. 11.

Still referring more specifically to Table 2, the flow characteristics may include a desiccation state within the wound dressing that also may be identified by the assessment of the pH data, the humidity data, and the temperature data along with contemporaneous wound pressure (WP) data, pump pressure (PP) data, and the pump duty cycle (PD) data. For example, a desiccation state may be identified if the pump pressure (PP) data and the pump duty cycle (PD) data remain unchanged, unless there is an air leak present which causes a moisture drop. In some embodiments, the desiccation state may be identified further if the wound pressure (WP) the also remains unchanged, unless there is an air leak present. In yet other embodiments, the desiccation state may be identified further if the humidity data decreases longitudinally over time. The humidity data may be tracked and compared to a minimum threshold value to prevent or avoid wound desiccation. The negative pressure control algorithm may be configured to provide an alert and/or an alarm in the event that the humidity data falls below the minimum threshold value. In still other embodiments, the desiccation state may be identified further if the pH data decreases slightly as the tissue site becomes slightly more acidic from drying. The temperature data also may change based on drying and the lack of sufficient exudation of the at the tissue site. Referring to FIG. 17 as an example, a graph is shown illustrating test results using the dressing interface 400 for the detection of desiccation conditions based on the assessment of humidity data over time generated by the negative pressure control algorithm of FIG. 11. The tissue interface such as, for example, tissue interface 108, was filled in saturated with simulated wound fluid. After the tissue interface was saturated with the wound fluid, the wound pressure (WP) was set as a target pressure (TP) of 125 mmHg and applied to the tissue interface. As can be seen, a desiccation state may be identified a decreasing dressing humidity 731 compared to the ambient humidity by tracking the humidity data and comparing it to a minimum threshold value as described above. In some embodiments, the negative pressure control algorithm 605 may generate a command to provide an alert 664 and shut down the pump 104, for example, until the desiccation can be corrected.

The assessments of the pH data at 652, the humidity data at 654, and the temperature data at 656 along with contemporaneous wound pressure (WP) data, pump pressure (PP) data, and the pump duty cycle (PD) data may be utilized to assess the health of the wound at 658 including, for example, the progression of wound healing, i.e., the wound status.

TABLE 3

| Inputs | Wound Status:<br>Wound Health/Progression |
|---|---|
| Wound Pressure (WP) | Critically affected<br>(May Increase or Decrease) |
| Wound Humidity (Hum) | May increase or decrease slowly |
| Wound pH | Will change with wound regression or progression<br>(May Increase or Decrease) |
| Wound Temperature (Temp) | May increase or decrease slowly |

Referring more specifically to Table 3, the wound status may include a determination of the progression of wound healing that may be identified by the assessment of the pH data, the humidity data, and the temperature data along with contemporaneous wound pressure (WP) data, pump pressure (PP) data, and the pump duty cycle (PD) data. For example, a wound healing state may be identified when the pH data changes in response to wound healing regression or progression. For example, in some embodiments, the wound may be considered in a healthy state if the wound fluids have a pH of approximately 7.4 and the pH data indicates that the pH has held at that value over a predetermined time period. In some other embodiments, the wound may be considered in a healthy state if the wound fluids have a pH that stays within a range from about 5.0 to about 8.0 and remains within that range over a predetermined time period. More specifically, if the pH data exceeds 8.0, the wound may be considered to be in a chronic state. Additionally, if the pH data is less than about 6.0, the wound may be considered to be in an inflammatory state. In some embodiments, the wound healing state may be identified when the humidity data and the temperature data both increase or decrease slowly at predetermined rates. For example, if the temperature data indicates that the temperature is increasing, the increasing temperature may be an indication that the wound is infected. Additionally, the wound pressure (WP) or the pump pressure (PP) may critically affect the healing progression or regression. For example, if the pressure is not within the therapeutic range that was prescribed, then the patient is not getting the benefit of the therapy. However, wound progression or regression does not necessarily affect the wound pressure (WP) or the pump pressure (PP). In some embodiments, the negative pressure control algorithm 605 may generate a command to provide an alert 665 and continue providing therapy including, for example, the instillation of fluids that may include medication until the pH returns to an acceptable range.

While shown in a few illustrative embodiments, a person having ordinary skill in the art will recognize that the systems, apparatuses, and methods described herein are susceptible to various changes and modifications. For example, certain features, elements, or aspects described in the context of one example embodiment may be omitted, substituted, or combined with features, elements, and aspects of other example embodiments. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 102, the container 112, or both may be eliminated or separated from other components for manufacture or sale. In other example configurations, the controller 110 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A system for controlling negative pressure therapy using properties of fluids at a tissue site, the system comprising:
    a dressing interface for coupling a source of negative-pressure to the tissue site, the dressing interface comprising:
        a housing having a therapy cavity and a component cavity sealed from the therapy cavity, wherein the therapy cavity includes an opening configured to be disposed in fluid communication with the tissue site, a negative-pressure port adapted to fluidly couple the therapy cavity to the source of negative-pressure, and a vent port adapted to fluidly couple the therapy cavity to a source of positive-pressure;
        a pressure sensor mounted to the housing in fluid communication with the therapy cavity and configured to sense the pressure of the fluids at the tissue site;
        a humidity sensor mounted to the housing in fluid communication with the therapy cavity and configured to sense the humidity of the fluids at the tissue site;
        a temperature sensor mounted to the housing in fluid communication with the therapy cavity and configured to sense the temperature of the fluids at the tissue site; and
        a processing element disposed within the component cavity and electrically coupled to the pressure sensor, the humidity sensor, and the temperature sensor within the component cavity for receiving property signals indicative of the pressure, humidity, and temperature of the fluid at the tissue site, the processing element being configured to determine flow characteristics of the system,
    wherein the flow characteristics of the system include at least one of a blockage state condition within the system, an air leak state within the system, a fluid leak state within the system, or a desiccation state within the system and wherein a controller is configured to provide an alarm indicative of at least one of the blockage state condition, the air leak state, the fluid leak state, or the desiccation state based on the property signals, a pump pressure, and a duty cycle.

2. The system of claim 1, wherein the pressure sensor, the humidity sensor, and the temperature sensor are disposed within the therapy cavity.

3. The system of claim 1, wherein the pressure sensor, the humidity sensor, and the temperature sensor are disposed outside the therapy cavity.

4. The system of claim 1, wherein the processing element further comprises a microprocessor and a transmitter and is configured to process and transmit the property signals for assessing the flow characteristics of the system.

5. The system of claim 4, wherein the controller is configured to receive the property signals from the processing element and is further configured to assess the flow characteristics of the system.

6. The system of claim 5, wherein the system is configured to be fluidly coupled to a pump for providing negative-pressure to the dressing interface and the tissue site, and wherein the system further comprises a sensor electrically coupled to the controller and adapted to determine a pump pressure being provided by the pump.

7. The system of claim 1, wherein the controller provides an alarm indicative of the blockage state condition when the temperature, the duty cycle, and the pump pressure increase.

8. The system of claim 7, wherein the controller provides an alarm indicative of the blockage state condition when the humidity increases.

9. The system of claim 1, wherein the controller provides an alarm indicative of the air leak state when the pump pressure and the duty cycle increase.

10. The system of claim 1, wherein the controller provides an alarm indicative of the fluid leak state when the humidity and temperature increase.

11. The system of claim 1, wherein the controller provides an alarm indicative of the desiccation state when the humidity decreases and the duty cycle increases.

12. The system of claim 1, wherein the dressing interface further comprises:
    a pH sensor mounted to the housing in fluid communication with the therapy cavity and configured to sense the pH of the fluids at the tissue site; and
    wherein the processing element is electrically coupled to the pH sensor for receiving property signals including a property signal indicative of the pH of the fluid at the tissue site, the processing element being further configured to assess a health characteristic of the tissue site.

13. The system of claim 12, wherein the pH sensor is disposed within the therapy cavity.

14. The system of claim 12, wherein the processing element further comprises a microprocessor and a transmitter and is configured to process and transmit the property signals for assessing the health characteristics of the tissue site.

15. The system of claim 14, wherein the system further comprises a controller for receiving the property signals from the processing element and is further configured to assess the health characteristics of the tissue site.

16. The system of claim 15, wherein the health characteristics of the system include a wound progression state within the system, and wherein the controller is configured to provide an alarm indicative of the wound progression state based on the property signals.

17. The system of claim 16, wherein the controller provides an alarm indicative of the wound progression state when the pH increases or decreases.

* * * * *